(12) United States Patent
Bowman

(10) Patent No.: US 11,710,542 B2
(45) Date of Patent: Jul. 25, 2023

(54) METHODS OF PROTEIN DOCKING AND RATIONAL DRUG DESIGN

(71) Applicant: Washington University, St. Louis, MO (US)

(72) Inventor: Gregory R. Bowman, St. Louis, MO (US)

(73) Assignee: Washington University, St. Louis, MO (US)

( * ) Notice: Subject to any disclaimer, the term of this patent is extended or adjusted under 35 U.S.C. 154(b) by 508 days.

(21) Appl. No.: 16/099,132

(22) PCT Filed: May 4, 2017

(86) PCT No.: PCT/US2017/031095
§ 371 (c)(1),
(2) Date: Nov. 5, 2018

(87) PCT Pub. No.: WO2017/192872
PCT Pub. Date: Nov. 9, 2017

(65) Prior Publication Data
US 2019/0147985 A1 May 16, 2019

Related U.S. Application Data

(60) Provisional application No. 62/332,172, filed on May 5, 2016.

(51) Int. Cl.
*G16C 20/50* (2019.01)
*G16B 15/00* (2019.01)
(Continued)

(52) U.S. Cl.
CPC ............... *G16C 20/50* (2019.02); *G06N 5/04* (2013.01); *G06N 7/01* (2023.01); *G16B 15/00* (2019.02);
(Continued)

(58) Field of Classification Search
CPC ........ G16C 20/50; G16C 20/30; G16C 20/70; G16C 60/00; G16B 15/00; G16B 15/30;
(Continued)

(56) References Cited

U.S. PATENT DOCUMENTS

| | | | |
|---|---|---|---|
| 2009/0018777 A1* | 1/2009 | Hrnciar | G16B 35/00 702/19 |
| 2013/0303387 A1* | 11/2013 | Sander | G16B 15/00 506/8 |
| 2013/0304433 A1* | 11/2013 | Zheng | G16B 15/30 703/2 |

FOREIGN PATENT DOCUMENTS

| | | |
|---|---|---|
| WO | 2017011779 A1 | 1/2017 |
| WO | 2017192872 A1 | 11/2017 |

OTHER PUBLICATIONS

Annis et al. "A general technique to rank protein-ligand binding affinities and determine allosteric versus direct binding site competition in compound mixtures", J. Am. Chem. Soc., Dec. 1, 2004;126(47):15495-503.*

(Continued)

*Primary Examiner* — Alexander Satanovsky
(74) *Attorney, Agent, or Firm* — Polsinelli PC

(57) ABSTRACT

Aspects of the present disclosure relate to computing systems and computational methods for docking a library of compounds against a massive amount of conformations of a protein of interest.

13 Claims, 23 Drawing Sheets
(21 of 23 Drawing Sheet(s) Filed in Color)

(51) Int. Cl.
G16B 20/50 (2019.01)
G16B 20/30 (2019.01)
G06N 7/01 (2023.01)
G06N 5/04 (2023.01)
G16C 20/30 (2019.01)
G16C 60/00 (2019.01)
G16C 20/70 (2019.01)
G16B 15/30 (2019.01)

(52) U.S. Cl.
CPC ............ G16B 15/30 (2019.02); G16B 20/30 (2019.02); G16B 20/50 (2019.02); G16C 20/30 (2019.02); G16C 20/70 (2019.02); G16C 60/00 (2019.02)

(58) Field of Classification Search
CPC .......... G16B 20/30; G16B 20/50; G06N 5/04; G06N 7/01
See application file for complete search history.

(56) References Cited

OTHER PUBLICATIONS

Arai et al., "A quantitative analysis to unveil specific binding proteins for bioactive compounds", Protein Engineering, Design & Selection vol. 26 No. 4 pp. 249-254, 2013.*
Barril, X., "Docking Points," Nat. Chem., Jul. 2014, pp. 560-561, vol. 6, Macmillan Publishers Limited.
Boehr, D. et al., "The Dynamic Energy Landscape of Dihydrofolate Reductase Catalysis," Sci., Sep. 2006, pp. 1638-1642, vol. 313, No. 5793.
Bowman, G. et al., "Progress and challenges in the automated construction of Markov state models for full protein systems," J. Chem. Physics, 2009, pp. 124101-1 to 124101-11, vol. 131.
Bowman, G. et al., "Using generalized ensemble simulations and Markov state models to identify conformational states," NIH Public Access Author Manuscript, Oct. 1, 2010, pp. 1-10, published in final edited form as: Methods, Oct. 2009, pp. 197-201, vol. 49, No. 2.
Bowman, G. et al., "Equilibrium fluctuations of a single folded protein reveal a multitude of potential cryptic allosteric sites," PNAS, Jul. 2012, pp. 11681-11686, vol. 109, No. 29.
Bowman, G., "An Overview and Practical Guide to Building Markov State Models," In: Bowman, G et al. (eds), "An Introduction to Markov State Models and Their Application to Long Timescale Molecular Simulation," Adv. Exp. Med. Biol., 2014, pp. 7-22, vol. 797, Springer, Dordrecht.
Bowman, G. et al., "Discovery of multiple hidden allosteric sites by combining Markov state models and experiments," PNAS, Mar. 2015, pp. 2734-2739, vol. 112, No. 9.
Bush, K. et al., "Updated Functional Classification of beta-Lactamases," Antimicrob. Agents Chemother., Mar. 2010, pp. 969-976, vol. 54, No. 3.
Cavasotto, C. et al., "Protein Flexibility in Ligand Docking and Virtual Screening to Protein Kinases," J. Mol. Biol., 2004, pp. 209-225, vol. 337, Elsevier Ltd.
Dellus-Gur, E. et al., "Negative Epistasis and Evolvability in TEM-1 beta-Lactamase—The Thin Line between an Enzyme's Conformational Freedom and Disorder," J. Mol. Biol., Jul. 2015, pp. 2396-2409, vol. 427, No. 14, Elsevier Ltd.
Fischer, M. et al., "Incorporation of protein flexibility and conformational energy penalties in docking screens to mprove ligand discovery," Nat. Chem., Jul. 2014, pp. 575-583, vol. 6, Macmillan Publishers Limited.
Fraser, J. et al., "Hidden alternative structures of proline isomerase essential for catalysis," Nature, Dec. 2009, pp. 569-673, vol. 462, with Methods, 1 pg., Macmillian Publishers Limited.
Friedland, I. et al., "Management of Infections Caused by Antibiotic-Resistant *Streptococcus pneumoniae*," Drug Ther., Aug. 1994, pp. 377-382, vol. 331, No. 6.
Hall, B., "Predicting Evolution by In Vitro Evolution Requires Determining Evolutionary Pathways," Antimicrob. Agents Chemother., Sep. 2002, pp. 3035-3038, vol. 46, No. 9.
Hart, K. et al., "Modelling proteins' hidden conformations to predict antibiotic resistance," Nat. Commun., 2016, pp. 1-10, vol. 7, No. 12965.
Hart, K. et al., "Designing small molecules to target cryptic pockets yields both positive and negative allosteric modulators," PLoS ONE, Jun. 2017, pp. 1-13, vol. 12, No. 6, e0178678.
Henzler-Wildman, K. et al., "Dynamic personalities of proteins," Nature, Dec. 2007, 964-972, vol. 450.
Huang, X. et al., "Rapid equilibrium sampling initiated from nonequilibrium data," PNAS, Nov. 2009, pp. 19765-19769, vol. 106, No. 47.
Huang, S-Y. et al., "Advances and Challenges in Protein-Ligand Docking," Int. J. Mol. Sci., 2010, pp. 3016-3034, vol. 11.
International Search Report and Written Opinion dated Jul. 31, 2017 from related Patent Application No. PCT/US2017/31095; 10 pgs.
Jain, A., "Surflex-Dock 2.1: robust performance from ligand energetic modeling, ring flexibility, and knowledge-based search," J. Comput. Aided Mol. Des., 2007, pp. 281-306, vol. 21, Springer Science+Business Media B.V.
Jelsch, C. et al., "Crystal Structure of *Escherichia coli* TEM1 beta-Lactamase at 1.8 A Resolution," Proteins, Aug. 1993, pp. 364-383, vol. 16, No. 4.
Kohlhoff, K. et al., "Cloud-based simulations on Google Exacycle reveal ligand modulation of GPCR activation pathways," Nat. Chem., 2014, pp. 15-21, vol. 6.
McGibbon, R. et al., "MDTraj: A Modern Open Library for the Analysis of Molecular Dynamics Trajectories," Biophysical Journal, Oct. 2015, pp. 1528-1532, vol. 109.
Motlagh, H. et al., "The ensemble nature of allostery," NIH Public Access Author Manuscript, Nov. 7, 2014, pp. 1-21, published in final edited form as: Nature, Apr. 17, 2014, pp. 331-339, vol. 508, No. 7496.
"Methods for Dilution Antimicrobial Susceptibility Tests for Bacteria that Grow Aerobically; Approved Standard-Ninth Edition," Clinical and Laboratory Standards Institute, Jan. 2012, pp. 1-68, vol. 32, No. 2, Document M07-A9.
Orencia, M. et al., "Predicting the emergence of antibiotic resistance by directed evolution and structural analysis," Nat. Struct. Biol., Mar. 2001, pp. 238-242, vol. 8, No. 3.
Plattner, N. et al., "Protein conformational plasticity and complex ligand-binding kinetics explored by atomistic simulations and Markov models," Nat. Commun., 2015, pp. 1-10, vol. 6, No. 7653, Macmillan Publishers Limited.
Salverda, M. et al., "Natural evolution of TEM-1 beta-lactamase: experimental reconstruction and clinical relevance," FEMS Microbiol. Rev., 2010, pp. 1015-1036, vol. 34, Blackwell Publishing Ltd.
Savard, P-Y. et al., "Backbone Dynamics of TEM-1 Determined by NMR: Evidence for a Highly Ordered Protein," Biochem., 2006, pp. 11414-11424, vol. 45, No. 38.
"What is ensemble docking and how can I use it?," Schrodinger LLC, Dec. 2016, Article ID 28, downloaded from https://www.schrodinger.com/kb/28; 3 pgs.
Strynadka, N. et al., "Molecular structure of the acyl-enzyme intermediate in beta-lactam hydrolysis at 1.7 A resolution," Nature, Oct. 22, 1992, pp. 700-705, vol. 359.
Tokuriki, N. et al., "Protein Dynamism and Evolvability," Sci., Apr. 2009, pp. 203-207, vol. 324, No. 5924.
Van Der Spoel, D. et al., "GROMACS: Fast, flexible, and Free," J. Comput. Chem., 2005, pp. 1701-1718, vol. 26, No. 16, Wiley Periodicals, Inc.
Wand, A., "The dark energy of proteins comes to light: conformational entropy and its role in protein function revealed by NMR relaxation," NIH Public Access Author Manuscript, Feb. 1, 2014, pp. 1-13, published in final edited form as Durr. Opin. Struct. Biol., Feb. 2013, pp. 75-81, vol. 23, No. 1.
Wandzik, I., "Current Molecular Docking Tools and Comparison Thereof," Match Commun. Math. Comput. Chem., 2006, pp. 271-278, vol. 55.

(56) References Cited

OTHER PUBLICATIONS

Webb, B. et al., "Comparative Protein Structure Modeling Using MODELLER," Curr. Protoc. Bioinform., Sep. 2014, pp. 5.6.1 to 5.6.32, vol. 47, John Wiley & Sons, Inc.
Weinreich, D. et al., "Darwinian Evolution Can Follow Only Very Few Mutational Paths to Fitter Proteins," Sci., Apr. 2006, pp. 111-114, vol. 312, No. 5770.
"Antimicrobial Resistance: Global Report on Surveillance," World Health Organization, 2014 Summary, 7 pgs.
Zaccolo, M. et al., "The Effect of High-Frequency Random Mutagenesis on in Vitro Protein Evolution: A Study on TEM-1 beta-Lactamase," J. Mol. Biol., 1999, pp. 775-783, vol. 285, Academic Press.
Zou, T. et al., "Evolution of Conformational Dynamics Determines the Conversion of a Promiscuous Generalist into a Specialist Enzyme," Mol. Biol. Evol., Oct. 13, 2014, pp. 132-143, vol. 32, No. 1, Oxford University Press.

* cited by examiner

METHODS OF PROTEIN DOCKING AND RATIONAL DRUG DESIGN

CROSS REFERENCE TO RELATED APPLICATIONS

This application claims the benefit of PCT Application PCT/US2017/31095, filed May 4, 2017, which claims priority from U.S. Provisional Application No. 62/332,172, filed May 5, 2016, the disclosures of which are hereby incorporated by reference in their entirety.

FIELD OF THE INVENTION

Aspects of the present disclosure relate to computing systems and computational methods for docking a library of compounds against a massive amount of conformations of a protein of interest.

BACKGROUND OF THE INVENTION

Most recent drug discovery programs have used high-throughput screens and rational drug design. While both approaches have had noteworthy successes, they also have limitations. For example, high-throughput screening can rapidly search through large libraries of chemicals for efficacious lead compounds but it is common for these screens to fail because chemical space is too large to explore exhaustively. In particular, it is easy to imagine a library that doesn't contain chemicals that bind different conformations a protein adopts and, therefore, never realizing these conformations exist. Rational drug design provides a more directed search by integrating information from crystallographic structures with the results of experimental tests of promising compounds to design small molecules that will bind tightly to specific sites. However, this strategy is limited by the information contained in the available crystal structures and may miss compounds that bind tightly to alternative structures.

Thus, there is a need in the art for a model that enhances the ability to identify and exploit the different structures a protein adopts thereby improving drug development and protein design.

BRIEF DESCRIPTION OF THE FIGURES

The application file contains at least one drawing executed in color. Copies of this patent application publication with color drawing(s) will be provided by the Office upon request and payment of the necessary fee.

(FIG. 2A) Overlay of TEM-1 (green, PDB 1BTL) and TEM-52 (yellow, PDB 1HTZ) reveal no major conformational differences. Residues at positions 104 and 238, which are proximal to the active site, are shown in pink sticks. Overlay of active site residues are shown for clarity (inset). (FIG. 2B) Docking scores for cefotaxime against single-structure homology models for each variant have no correlation with the measured catalytic efficiencies ($k_{cat}/K_m$). Error bars are standard errors from the fit.

(FIG. 3A) The crystal structure of TEM-1 (blue) is overlaid with a representative structure from MD simulations (red) that highlights large structural rearrangements in the Ω-loop. Residues E104 and G238 are shown in spheres. (FIG. 3B) There is a strong correlation (R=0.83) between the predicted populations of cefotaximase states and the measured catalytic efficiencies ($k_{cat}/K_m$). The correlation is robust to omitting any single data point (R≥0.51). Double mutants are shown in blue, and single mutants are shown in red. (FIG. 3C) There is a correlation (R=0.35) between the ensemble-docking scores for cefotaxime and the measured catalytic efficiencies ($k_{cat}/K_m$). (FIG. 3D) Cefotaxime $k_{cat}/K_m$ values reveal that substitutions at position 104 have similar effects in the wild-type and G238S backgrounds. Error bars are standard errors from the fit. Computational errors are not shown for clarity as they are less than $3 \times 10^{-3}$ for both FIG. 3B and FIG. 3C.

(FIG. 4A) There is a strong correlation between the in vitro and in vivo activities against CFX. (FIG. 4B) There is a weaker correlation between the in vitro and in vivo activities against BP, which may be due to the fact that the variants behave more similarly to one another overall against this substrate. (FIG. 4C) There is a strong correlation between the populations of cefotaximase states in simulations and in vitro activities against CFX. The populations of the cefotaximase states for some of the single mutants are high compared to some of the double mutants, because the reduction in Ω-loop motion on the side near residue 104 is greater than on the side near 238, so the RMSD-based clustering is more sensitive to these changes. (FIG. 4D) There is a weaker correlation between the populations of penicillinase states in simulations and in vitro activities against BP. Because we did not study any enzymes with low activity against benzylpenicillin, it is more difficult to pinpoint which states are responsible for penicillinase activity. (FIG. 4E) E104A and E104R have comparable effects on cefotaximase activity in the wild-type and G238S backgrounds, while E104M and E104K appear to have epistasis with G238S. E104M has negative epistasis (it is more effective at increasing cefotaximase activity on its own than when it is paired with G238S), while E104K has positive epistasis (it is more effective at increasing cefotaximase activity when paired with G238S). Both substitutions are capable of improving activity by ~10-fold, but the presence or absence of other mutations are important for these effects to manifest. A dotted line at y=1 indicates where activity is equal between the variant and parent sequence. (FIG. 4F) Most substitutions at 104 have negative or no impact on penicillinase activity with the exception of E104M. On its own, this substitution increases activity against BP and CFX. Why this variant has not been observed in nature is the subject of ongoing studies.

(FIG. 5A) The distribution of distances between position 104 and 167 of the Ω-loop shows that states with a short distance are more probable in variants containing the E104K substitution. (FIG. 5B) A representative structure from simulations containing the G238S substitution reveals a hydrogen bond between the side chain of S238 and backbone carbonyl of N170.

FIG. 7 depicts a graph showing that relaxation timescales for TEM-1 establish the model satisfies the Markov assumption. Relaxation timescales are shown for lag times from 1 to 20 ns. Both axes are in ns. The flatness of the plots suggests the model satisfies the Markov assumption for lag times as small as 1 ns. The relaxation timescales for the other variants are qualitatively similar.

DETAILED DESCRIPTION OF THE INVENTION

Aspects of the present disclosure involve a ranking system and corresponding computational method to automatically (e.g., in real-time) rank two or more compounds that interact with a protein of interest. In various aspects, the computational method, executable by the ranking system, generally comprises: (a) automatically determining the different conformations a protein adopts; (b) quantifying the relative probabilities that the protein adopts each of the conformations; (c) executing logic that docks each compound against each conformation; (d) automatically calculating an average score for each compound, wherein the score is weighted by the probability the protein adopts the conformation; and (e) automatically generating an output, such as a list of ranked compounds that effectively interact with the protein.

Figure 1:
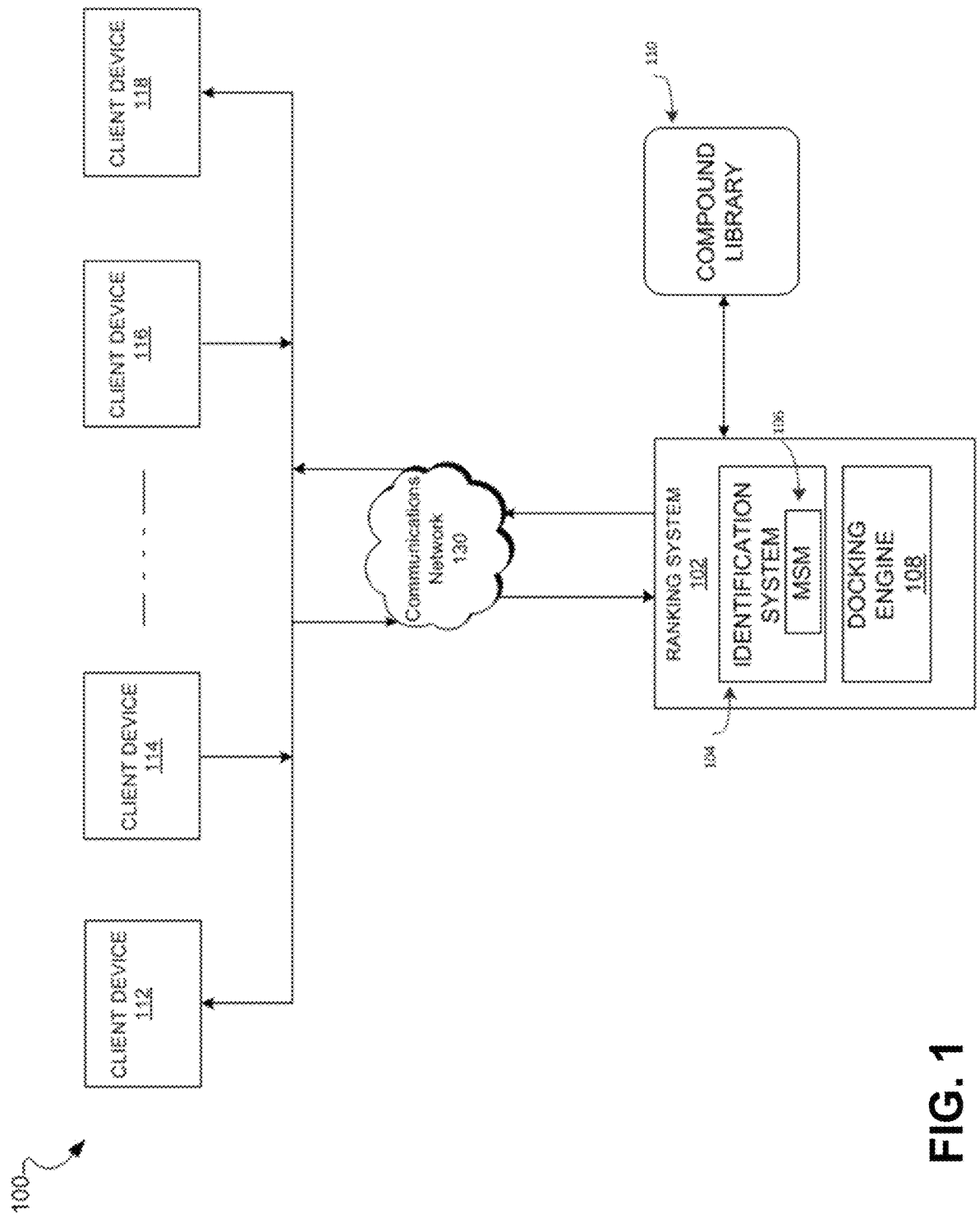
FIG. 1 is a block diagram of a computing architecture for performing various aspects of the present disclosure.

FIG. 1 illustrates a computing architecture 100 that may be used to rank various compounds that interact with a protein of interest, according to one embodiment. As illustrated, the computing architecture 100 includes a ranking system distributed throughout and/or otherwise accessible (i.e., networked) via a communications network 130 (e.g., a cloud computing arrangement), which may be an IP-based telecommunications network, the Internet, an intranet, a local area network, a wireless local network, a content distribution network, or any other type of communications network, as well as combinations of networks. The ranking system 102 automatically ranks compound(s) that interact with a protein of interest and generates some form of output (e.g., a structure document) that identifies a compound according to its corresponding ranking, for display at one or more client devices 112-118, which may be any of, or any combination of, a personal computer; handheld computer; mobile phone; digital assistant; smart phone; server; application; and the like.

In some embodiments, the ranking system 102 includes: 1) an identification engine 104 that automatically determines and/or identifies protein confirmations; and 2) a docking engine 108 that automatically performs a weighted ranking of the compounds with the identified protein confirmations.

I. Protein Conformations

Referring again to FIG. 1, the identification system 104 automatically identifies and/or otherwise determines thousands of potential confirmations a protein of interest can adopt. A protein of interest, as used herein, can be any polypeptide that adopts a tertiary structure. Based on the thermodynamics and kinetics of each identified confirmation, the identification system 104 automatically calculates and/or otherwise quantifies the relative probability that the protein of interest will adopt a given confirmation.

In some embodiments, the identification engine 104 may include a Markov State Model ("MSM") detector 106 that generates quantitative maps of the different structures that a protein can adopt. Generally speaking, MSMs are stochastic signal models that use definable parameters to model randomly changing systems where it is assumed that future states depend only on the present state and not on the sequence of events that preceded it. In the context of protein adoptions, the MSMs generated by the MSM unit 106 may be constructed using atomically-detailed molecular dynamics simulations to identify the structural states a protein populates, their equilibrium probabilities, and the rates of transitioning between them. In one specific example, the MSMs may be constructed using a crystal structure of wild-type and a homology model of a mutated version of the wild-type protein as starting points for 2.5 microseconds of explicit-solvent molecular dynamics simulations per sequence. MSMBuilder (Bowman et al. *Methods* 2009; 49: 197-201, the disclosure of which is hereby incorporated by reference in its entirety) was used to cluster both datasets based on the RMSD of shared residues in the active site and then the equilibrium thermodynamics and kinetics of each sequence was determined independently in this shared state space.

In some embodiments, the MSM detector 106 may determine and/or quantify hidden conformations. As used herein, hidden confirmations are confirmations that are invisible to standard structural techniques. The inclusion of hidden confirmations may improve the predictive power of the effectiveness of a compound at binding to a protein of interest. In addition to improving predictions against known target sites, the identification of hidden confirmations facilitates the identification of cryptic sites. As used herein, cryptic sites are pockets that are not present in a protein's ligand-free crystal structure but open when the protein fluctuates away from its ground-state structure. Cryptic sites can exert allosteric control over the protein's activity.

Using this methodology, tens to hundreds of thousands or more confirmations may be identified for a single protein of interest. For example, more than 10 different conformations may be identified for a single protein of interest. Accordingly, more than 10, more than 15, more than 20, more than 25, more than 50, more than 75, more than 100, more than 125, more than 150, more than 175, more than 200, more than 300, more than 400, more than 500, more than 600, more than 700, more than 800, more than 900, more than 1000, more than 1500, more than 2000, more than 2500, more than 3000, more than 3500, more than 4000, more than 4500, more than 5000, more than 6000, more than 7000, more than 8000, more than 9000, more than 10,000, more than 11,000, more than 12,000, more than 13,000, more than 14,000, more than 15,000, more than 16,000, more than 17,000, more than 18,000, more than 19,000, more than 20,000, more than 30,000, more than 40,000, more than 50,000, more than 60,000, more than 70,000, more than 80,000, more than 90,000, more than 100,000, more than 150,000, more than 200,000, more than 250,000, more than 300,000, more than 350,000, more than 400,000, more than 450,000, or more than 500,000 different conformations may be identified for a single protein of interest. The number of different conformations identified is dependent upon the protein of interest. Without wishing to be bound by theory, a larger protein of interest is likely to have more conformations relative to a smaller protein of interest. In a specific embodiment, about 1000 to about 6000 different conformations may be identified for a single protein of interest.

II. Compound Docking

Referring again to FIG. 1, the ranking system 102 also includes the docking engine 108. More specifically, following the identification of the various conformations a protein adopts (e.g., via the identification system 104), the docking engine 108 accesses a compound library 110 containing a collection of two or more isolated compounds, pools of compounds, or combinations thereof, all of which are of sufficiently diverse structure. More specifically, the docking engine 108 automatically accesses the compound library 110 containing the various compounds of sufficiently diverse structure, such that at least one compound will bind to the protein of interest at a certain affinity level. Accordingly, the docking engine 108 automatically "docks" each compound of the compound library 110 against each identified conformation in the protein of interest. In one embodiment, the compound library 110 may be a database, data store, and/or some other type of storage device capable of storing or otherwise maintaining compound data identifying compounds. Although the compound library of FIG. 1 is depicted outside of the ranking system 102, it is contemplated that it may be local to the ranking system 102, or elsewhere.

As used herein, a compound may be a peptide, peptidomimetic, small molecule or drug. A compound library is a collection of more than 1 compound usually used for high-throughput screening. A compound library may be diverse oriented, Drug-like, Lead-like, peptide-mimetic, Natural Product-like, and/or Targeted against a specific family of biological targets such as Kinases, GPCRs, Proteases, PPI. Compound libraries are known in the art. Non-limiting examples of compound libraries include Selleckchem.com bioactive screening libraries, LOPAC® compound library, SoftFocus® compound library, TargetMol bioactive screening libraries, Aurora chemical compound libraries, ChemBridge screening libraries, the National Cancer Institute (NCI) Developmental Therapeutics library.

In one particular embodiment, the docking engine 108 may employ a Boltzmann docking process that approximates a given compound's relative binding affinities by calculating the ensemble-average score across all of the structural states, weighting each state by its equilibrium probability.

Once each compound in a library of compounds has been automatically docked against each automatically determined different conformation in the protein of interest, an average score for each compound is automatically calculated. The score is weighted by the probability the protein adopts the conformation. Accordingly, the average score is the relative binding affinity of the compound to the protein of interest when taking all conformations into account. Specifically, the average score is automatically calculated using the formula:

$$s_{final}(pocket,mol) = \Sigma_{struct} p(struct) \times s(struct,pocket,mol)$$

wherein:
  struct is a single conformation,
  pocket is a pocket in the single conformation,
  mol is a compound,
  p(struct) is the probability that the protein adopts the single conformation, and
  $s_{final}$(pocket,mol) is a final score for the compound that captures the average affinity across the different conformations of a pocket observed.

Once an average score for each compound is automatically calculated, a list of ranked compounds that effectively interact with the protein is automatically generated. Compounds that effectively interact with the protein may bind to any site on a protein, including an active site, protein-ligand interaction site, or cryptic pocket on the protein of interest. Compounds that bind one or more structures of a known active site may serve as competitive inhibitors that block binding of the substrate. Accordingly, as used herein, a competitive inhibitor is a compound that binds to the active site of the protein of interest and prevents binding of the substrate to the protein of interest. If the compound is determined to bind to an allosteric site, the compound may be deemed an allosteric inhibitor or allosteric activator. If the compound is determined to bind to an allosteric site in a hidden conformation, the compound may be deemed a cryptic inhibitor or a cryptic activator. As used herein, an allosteric inhibitor modifies the active site of a protein of interest so that substrate binding is reduced or prevented. In certain embodiments, an allosteric inhibitor induces a conformational change that changes the shape of the active site and reduces the affinity of the protein of interest's active site for its substrate. As used herein, an allosteric activator modifies the active site of a protein of interest so that the affinity for the substrate increases. In certain embodiments, an allosteric activator induced a conformational change that changes the shape of the active site and increases the affinity of the protein of interest's active site for its substrate.

Figure 12:
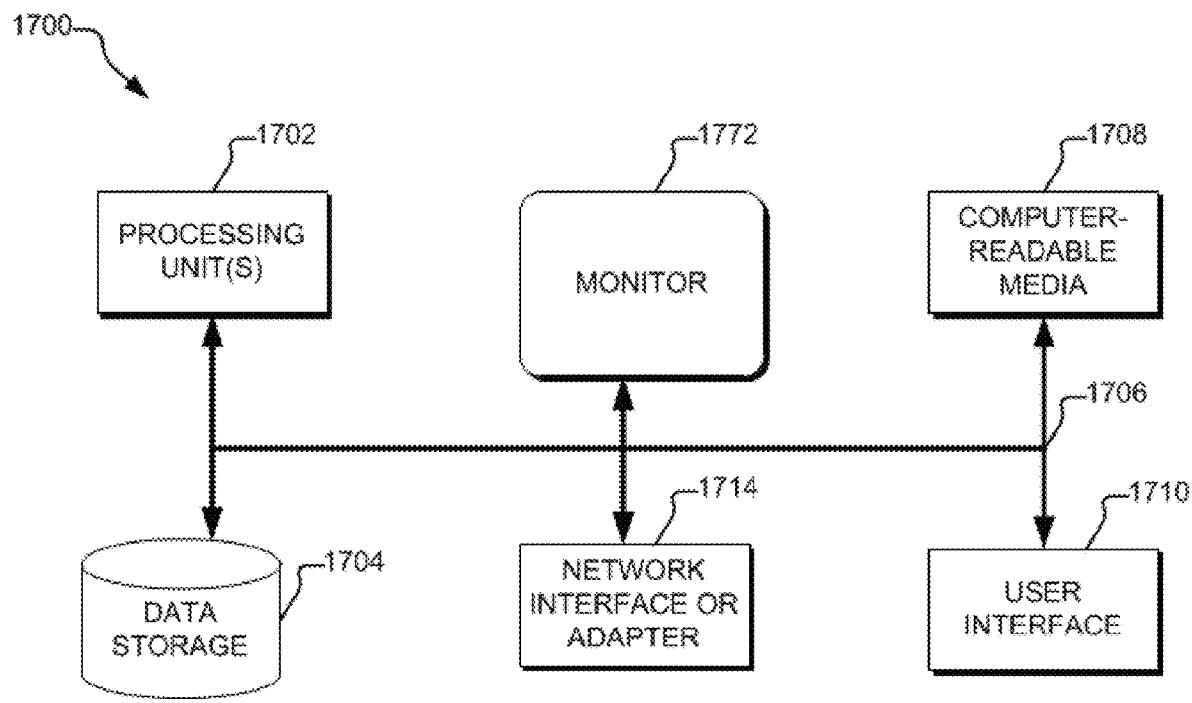
FIG. 12 is a block diagram of a computing device for performing various aspects of the present disclosure.

FIG. 12 illustrates an example of a suitable computing and networking environment 300 that may be used to implement various aspects and/or components of the present disclosure, particularly the computing components described in FIG. 1 (e.g., the ranking system 102). As illustrated, the computing and networking environment 1700 includes a general purpose computing device 1700, although it is contemplated that the networking environment 1700 may include one or more other computing systems, such as personal computers, server computers, hand-held or laptop devices, tablet devices, multiprocessor systems, microprocessor-based systems, set top boxes, programmable consumer electronic devices, network PCs, minicomputers, mainframe computers, digital signal processors, state machines, logic circuitries, distributed computing environments that include any of the above computing systems or devices, and the like.

Components of the computer 1700 may include various hardware components, such as a processing unit 1702, a data storage 1704 (e.g., a system memory), and a system bus 1706 that couples various system components of the computer 1700 to the processing unit 1702. The system bus 1706 may be any of several types of bus structures including a memory bus or memory controller, a peripheral bus, and a local bus using any of a variety of bus architectures. For example, such architectures may include Industry Standard Architecture (ISA) bus, Micro Channel Architecture (MCA)

bus, Enhanced ISA (EISA) bus, Video Electronics Standards Association (VESA) local bus, and Peripheral Component Interconnect (PCI) bus also known as Mezzanine bus.

The computer 1700 may further include a variety of computer-readable media 1708 that includes removable/non-removable media and volatile/nonvolatile media, but excludes transitory propagated signals. Computer-readable media 1708 may also include computer storage media and communication media. Computer storage media includes removable/non-removable media and volatile/nonvolatile media implemented in any method or technology for storage of information, such as computer-readable instructions, data structures, program modules or other data, such as RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium that may be used to store the desired information/data and which may be accessed by the computer 1700. Communication media includes computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. For example, communication media may include wired media such as a wired network or direct-wired connection and wireless media such as acoustic, RF, infrared, and/or other wireless media, or some combination thereof. Computer-readable media may be embodied as a computer program product, such as software stored on computer storage media.

The data storage or system memory 1704 includes computer storage media in the form of volatile/nonvolatile memory such as read only memory (ROM) and random access memory (RAM). A basic input/output system (BIOS), containing the basic routines that help to transfer information between elements within the computer 1700 (e.g., during start-up) is typically stored in ROM. RAM typically contains data and/or program modules that are immediately accessible to and/or presently being operated on by processing unit 1702. For example, in one embodiment, data storage 1704 holds an operating system, application programs, and other program modules and program data.

Data storage 1704 may also include other removable/non-removable, volatile/nonvolatile computer storage media. For example, data storage 1704 may be: a hard disk drive that reads from or writes to non-removable, nonvolatile magnetic media; a magnetic disk drive that reads from or writes to a removable, nonvolatile magnetic disk; and/or an optical disk drive that reads from or writes to a removable, nonvolatile optical disk such as a CD-ROM or other optical media. Other removable/non-removable, volatile/nonvolatile computer storage media may include magnetic tape cassettes, flash memory cards, digital versatile disks, digital video tape, solid state RAM, solid state ROM, and the like. The drives and their associated computer storage media, described above and illustrated in FIG. 12, provide storage of computer-readable instructions, data structures, program modules and other data for the computer 1700.

A user may enter commands and information through a user interface 1710 or other input devices such as a tablet, electronic digitizer, a microphone, keyboard, and/or pointing device, commonly referred to as mouse, trackball or touch pad. Other input devices may include a joystick, game pad, satellite dish, scanner, or the like. Additionally, voice inputs, gesture inputs (e.g., via hands or fingers), or other natural user interfaces may also be used with the appropriate input devices, such as a microphone, camera, tablet, touch pad, glove, or other sensor. These and other input devices are often connected to the processing unit 1702 through a user interface 1710 that is coupled to the system bus 1706, but may be connected by other interface and bus structures, such as a parallel port, game port or a universal serial bus (USB). A monitor 1712 or other type of display device is also connected to the system bus 1706 via an interface, such as a video interface. The monitor 1712 may also be integrated with a touch-screen panel or the like.

The computer 1700 may operate in a networked or cloud-computing environment using logical connections of a network interface or adapter 1714 to one or more remote devices, such as a remote computer. The remote computer may be a personal computer, a server, a router, a network PC, a peer device or other common network node, and typically includes many or all of the elements described above relative to the computer 1700. The logical connections depicted in FIG. 17 include one or more local area networks (LAN) and one or more wide area networks (WAN), but may also include other networks. Such networking environments are commonplace in offices, enterprise-wide computer networks, intranets and the Internet.

When used in a networked or cloud-computing environment, the computer 1700 may be connected to a public and/or private network through the network interface or adapter 1714. In such embodiments, a modem or other means for establishing communications over the network is connected to the system bus 1706 via the network interface or adapter 1714 or other appropriate mechanism. A wireless networking component including an interface and antenna may be coupled through a suitable device such as an access point or peer computer to a network. In a networked environment, program modules depicted relative to the computer 1700, or portions thereof, may be stored in the remote memory storage device.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Predicting Antibiotic Resistance by Modeling Hidden Conformations of Proteins Antibiotic resistance is a global health threat that results in millions of deaths and billions of dollars in healthcare costs every year. Expression of the enzyme TEM β-lactamase is the predominant mechanism underlying antibiotic resistance in pathogenic Gram-negative bacteria. TEM can quickly evolve the ability to degrade new drugs, but how changes in sequence alter its specificity remains a mystery despite decades of structural and biochemical research. Here, Markov state models (MSMs) were employed to map the distribution of structures that β-lactamases adopt, thus providing insight into hidden conformations that determine these enzymes' specificities that are not apparent from single "snap-shot" structures. It was discovered that clinical mutations conferring drug resistance act by shifting populations of functionally important states and/or altering interactions not always apparent from crystal structures. To demonstrate the utility of this approach, a number of novel mutations that confer β-lactamase with the ability to hydrolyze third-generation cephalosporins but have not yet been observed in nature were predicted and experimentally confirmed. These results establish a role for conformational heterogeneity, even in a supposedly rigid enzyme. This new framework for understanding drug resistance has great potential for numerous applications in drug and protein design.

Figure 2A:
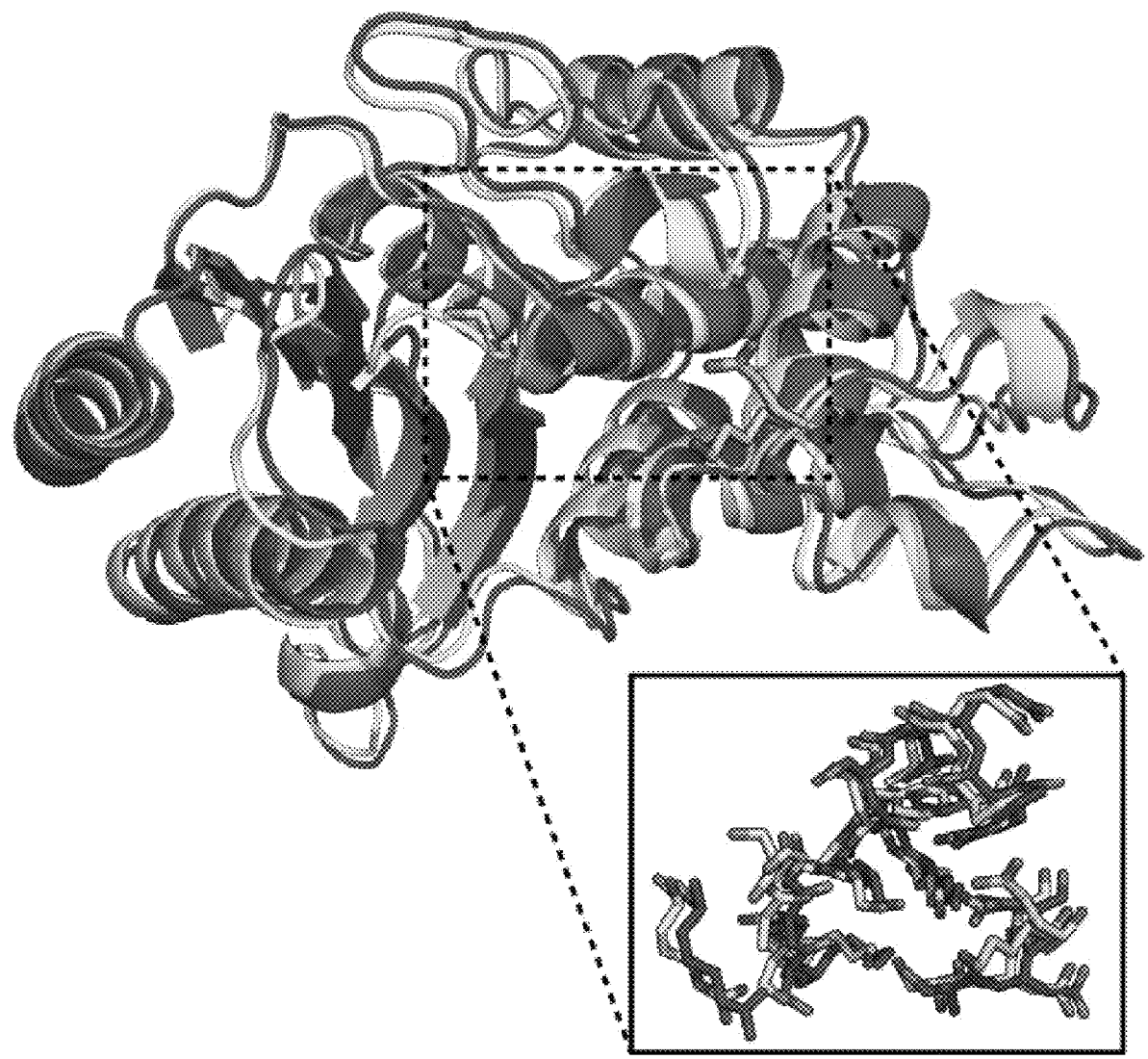
FIG. 2A and FIG. 2B depict a ribbon diagram and graph showing that single structures fail to predict the effects of mutations on β-lactamase's specificity.
Figure 2B:
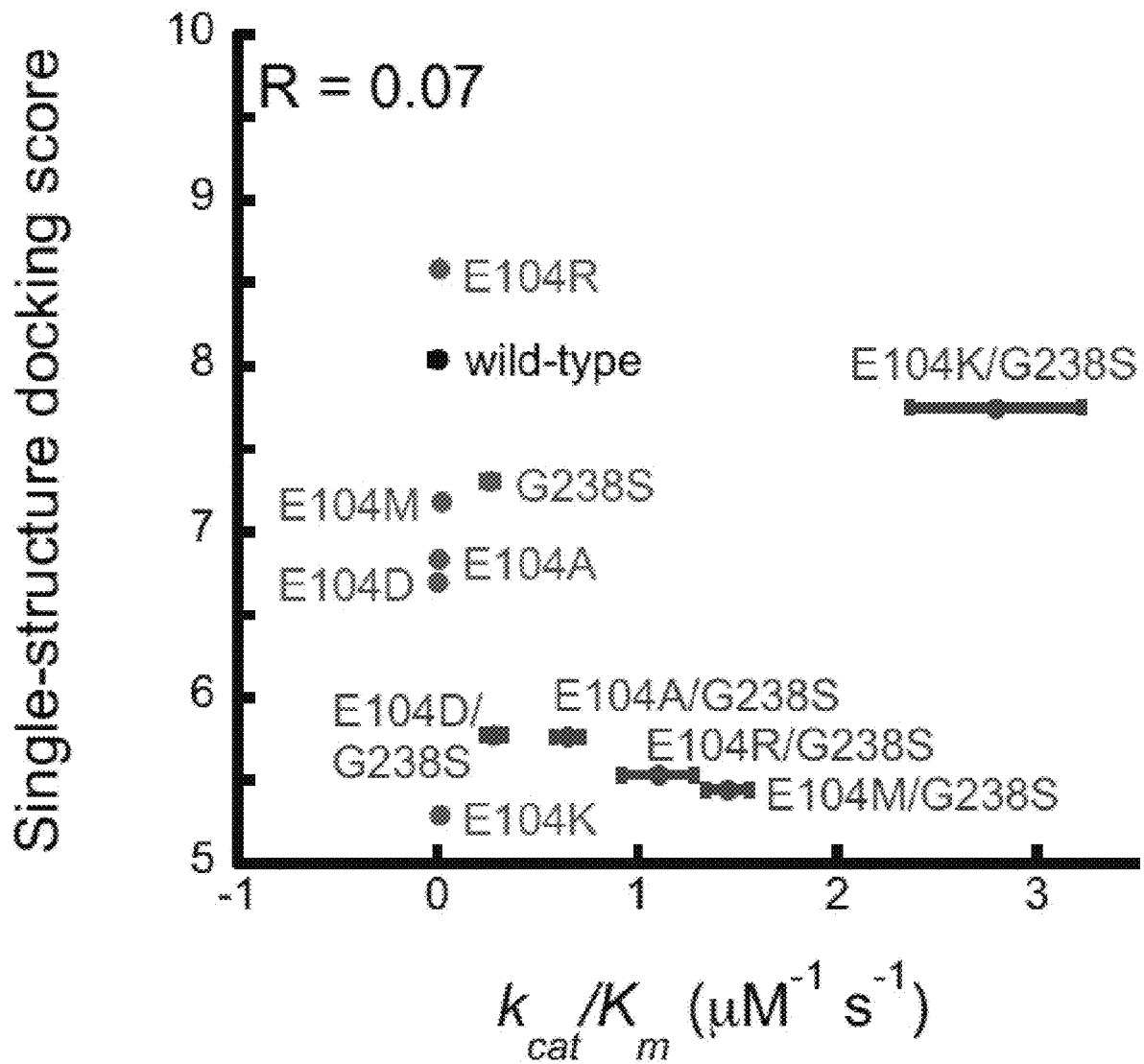

Solving crystal structures has been one main strategy for understanding how mutations alter β-lactamase's specificity. However, the differences between crystal structures of TEM variants with dramatically different specificities are extremely subtle. For example, the active sites of the TEM-1 and TEM-52 (E104K/G238S/M182T) β-lactamases are essentially identical (RMSD=0.35 Å) despite the fact that TEM-52 hydrolyzes a third-generation cephalosporin, cefotaxime, 2300-fold more efficiently than TEM-1 (FIG. 2A). Proposed mechanisms for altered substrate specificity largely focus on direct interactions between mutated residues and the new substrates, but many substitutions are too far from the active site to justify these explanations. Applying computational drug design tools to these structures also fails to reveal differences between their substrate specificities (FIG. 2B). Such failures are often attributed to shortcomings in the "force field" that these tools use to describe atomic interactions. However, they could also be interpreted as evidence for the inadequacy of focusing on single, rigid structures when it is known that proteins actually adopt a distribution of different structures at thermal equilibrium. These structures are referred to as hidden conformations, because they are invisible to standard structural techniques.

It was hypothesized that these hidden conformations are the missing ingredients required to connect protein structure with function and to predict the effect of mutations. This hypothesis is supported by computational models and room-temperature crystals that have revealed β-lactamases adopts diverse structures. A growing body of work also argues for the importance of conformational heterogeneity in processes like allostery, ligand binding, and catalysis.

To explore the role of conformational heterogeneity in enzyme specificity, a cefotaxime-degrading variant, E104K/G238S, was compared with a wild-type reference, TEM-1. E104K/G238S hydrolyzes cefotaxime 1400-fold more efficiently than wild-type, and *E. coli* expressing this variant have a >500-fold increase in their minimum inhibitory concentration (MIC) (Table 1). It has been suggested that the G238S substitution was acquired first during evolution, because this single variant has an MIC of 1.13 μM while E104K alone has little effect. Numerous models have been proposed for how these substitutions alter TEM's specificity. It has been proposed, for instance, that they form direct interactions with the oxyimino group of third-generation cephalosporins and that G238S opens up the active site to better accommodate the larger substrates.

To determine if the E104K/G238S double mutant alters the specificity of β-lactamase by modulating the probabilities of hidden conformations rather than simply altering the lowest energy conformation, MSMs for both wild-type and E104K/G238S were constructed. An MSM is essentially a map of the ensemble of structures that a protein adopts. These models are constructed by using atomically-detailed molecular dynamics simulations to identify the structural states a protein populates, their equilibrium probabilities, and the rates of transitioning between them. Here, MSMs were constructed by using the crystal structure of wild-type and a homology model of E104K/G238S as starting points for 2.5 microseconds of explicit-solvent molecular dynamics simulations per sequence. MSMBuilder (Bowman et al. *Methods* 2009; 49: 197-201) was used to cluster both datasets based on the RMSD of shared residues in the active site and then the equilibrium thermodynamics and kinetics of each sequence was determined independently in this shared state space.

Figure 3A:
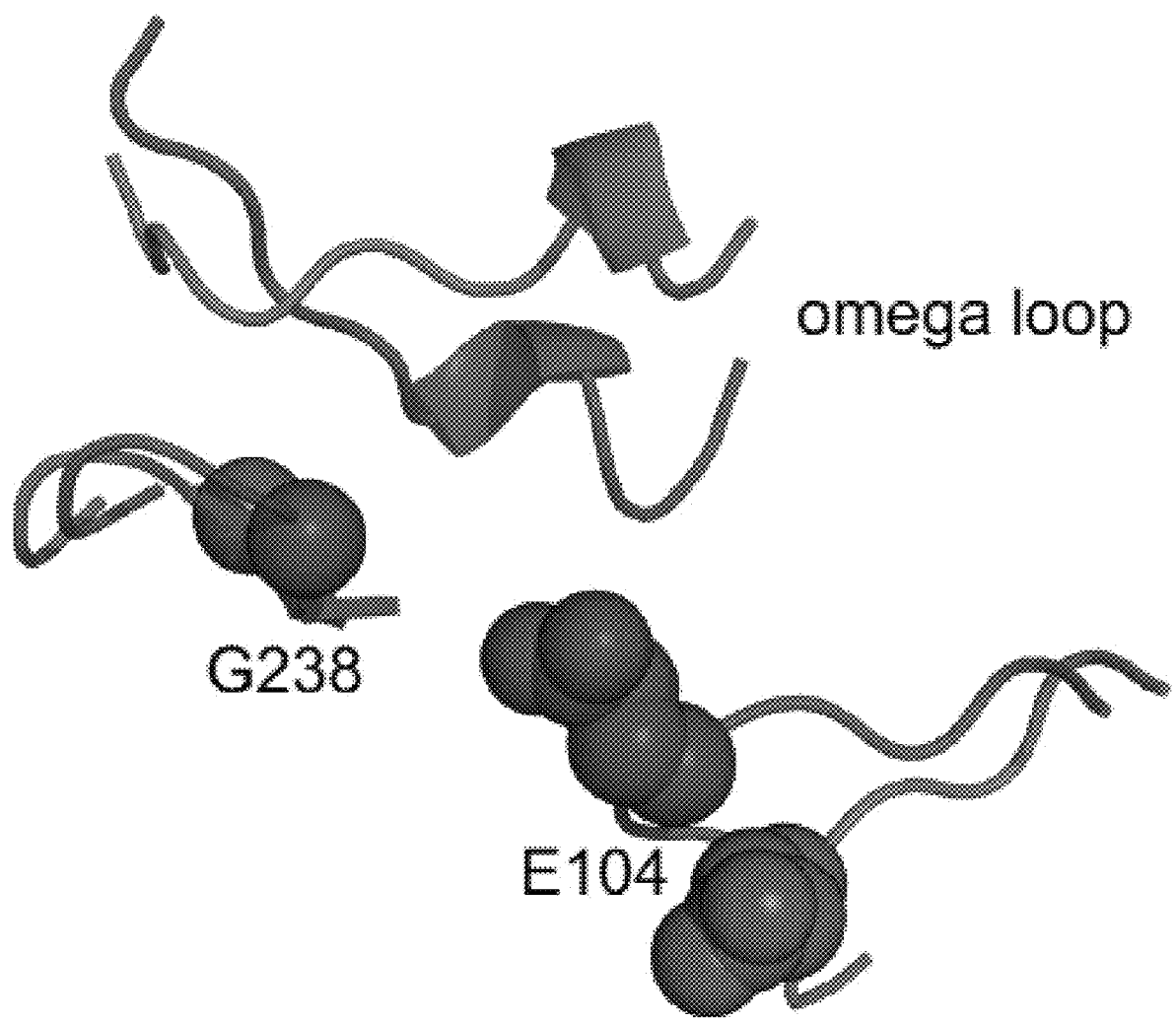
FIG. 3A, FIG. 3B, FIG. 3C and FIG. 3D depict a ribbon diagram and graphs showing an ensemble perspective predicts the effects of mutations on β-lactamase's specificity.

The MSMs were queried for states that are significantly more populated by one sequence over the other. This analysis reveals that the Ω-loop of wild-type undergoes substantial rearrangements that are absent in E104K/G238S (FIG. 3A). This loop is of known importance, because it interacts directly with the substrate, helps to coordinate a water required for catalysis, and is extremely sensitive to mutation. In vitro activity assays reveal that E104K/G238S has both a lower $K_m$ and higher $k_{cat}$ than wild-type (Table 2), suggesting that reduced 0-loop heterogeneity increases cefotaxime hydrolysis. This observation runs counter to a common assumption that more promiscuous enzymes have greater heterogeneity in their active sites.

Figure 3B:
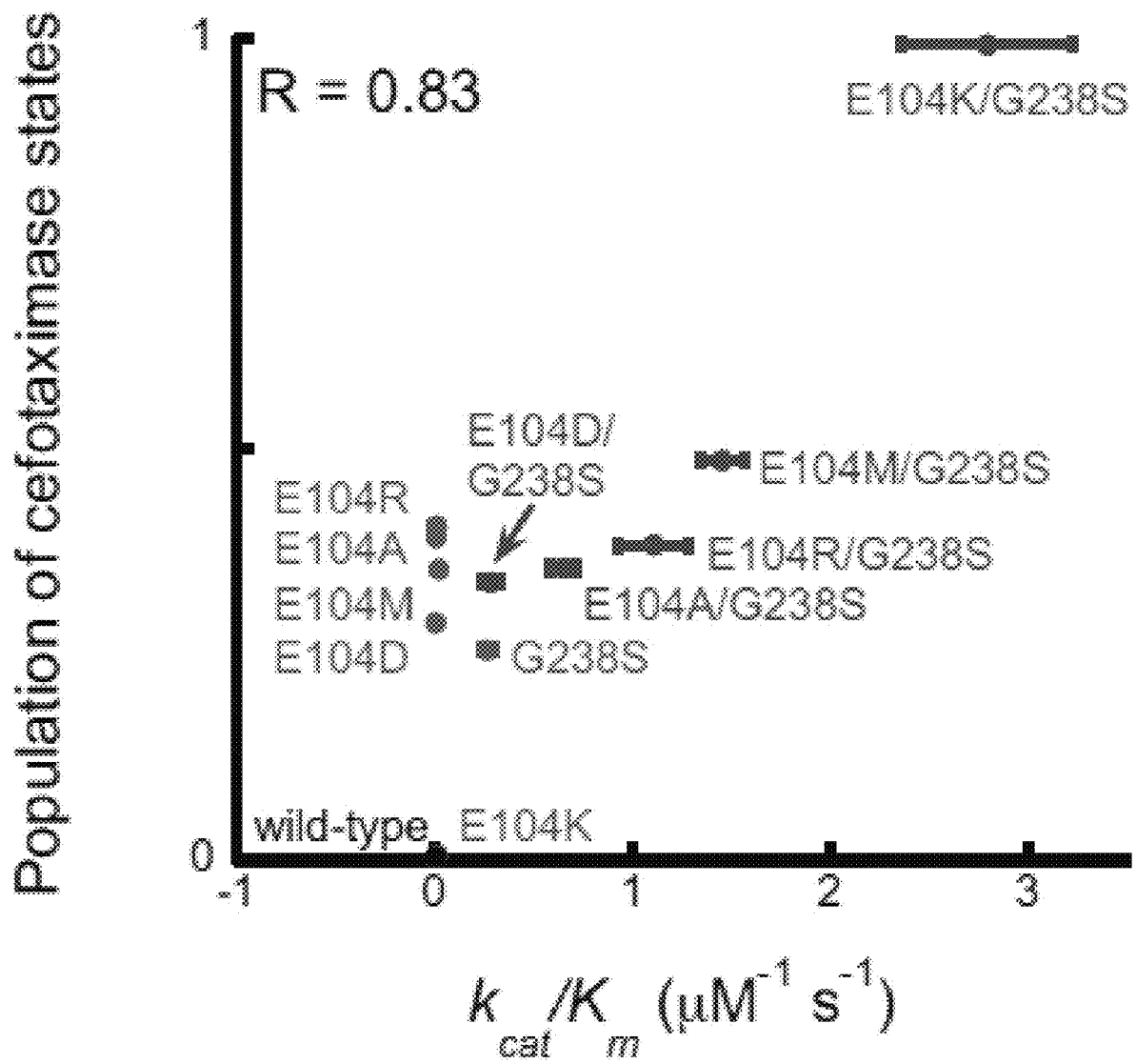
Figure 4A:
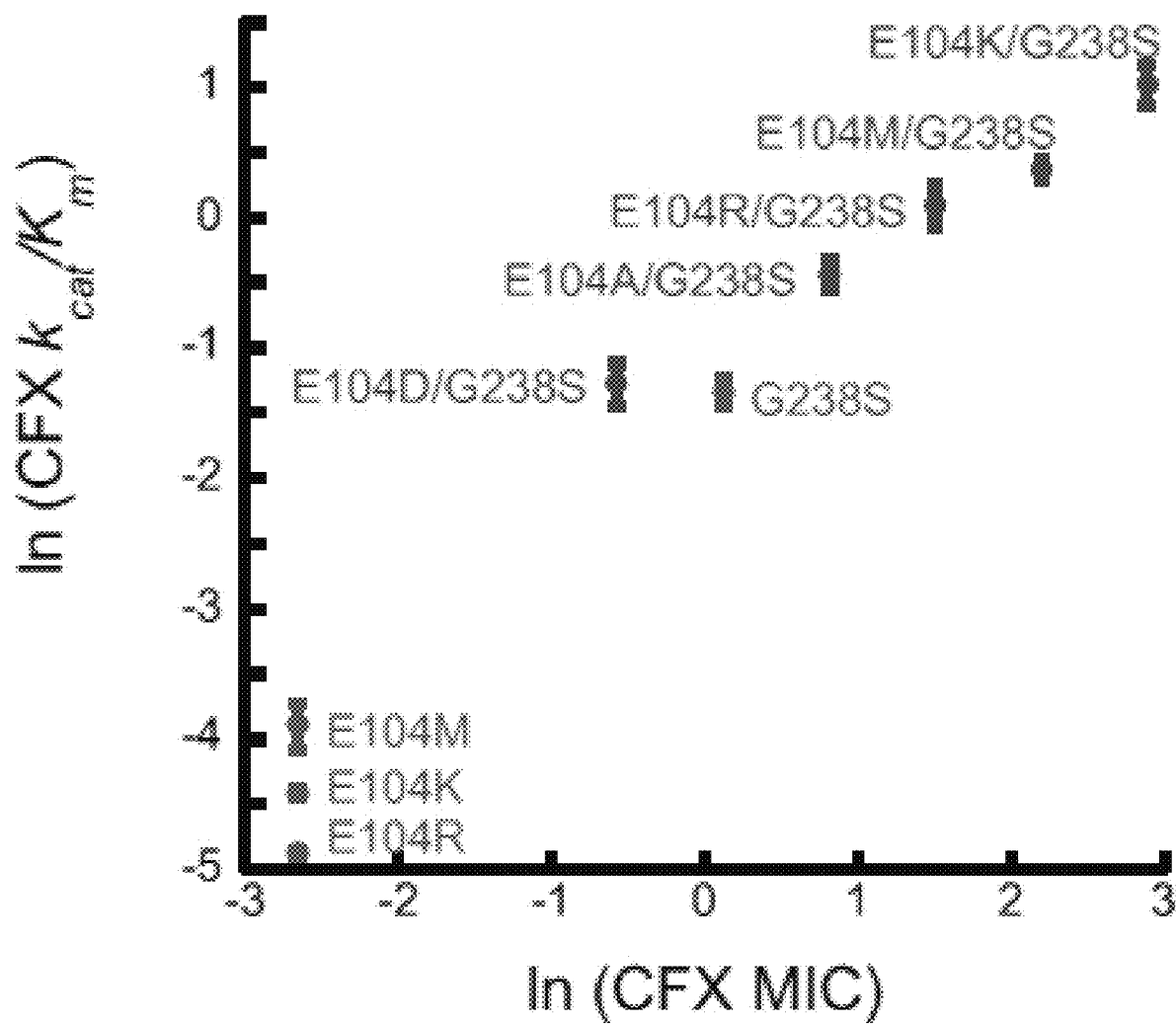
FIG. 4A, FIG. 4B, FIG. 4C, FIG. 4D, FIG. 4E and FIG. 4F depict graphs showing enzymes assayed for activity against both cefotaxime and benzylpenicillin in silico, in vitro and in vivo.
Figure 4B:
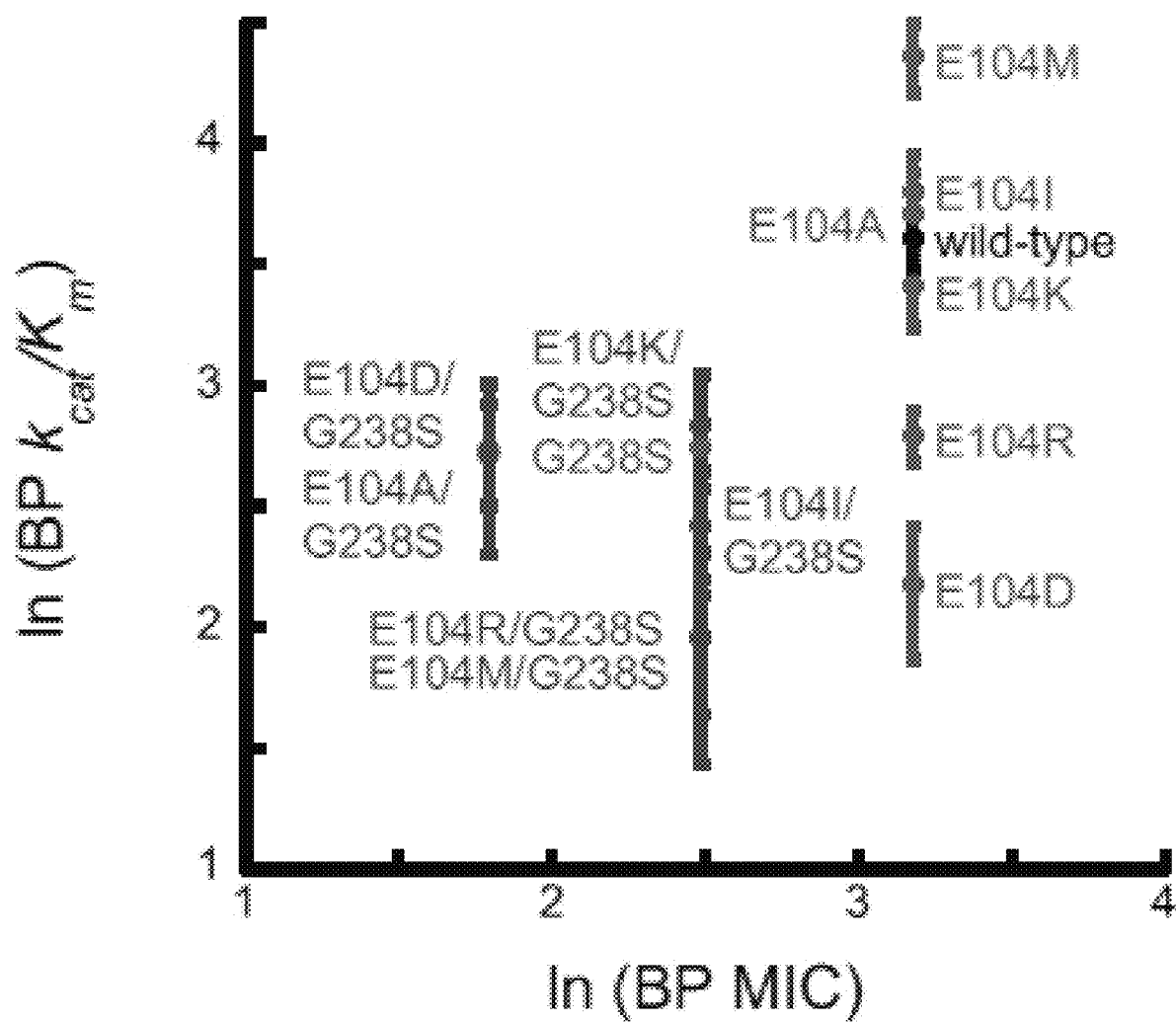
Figure 4C:
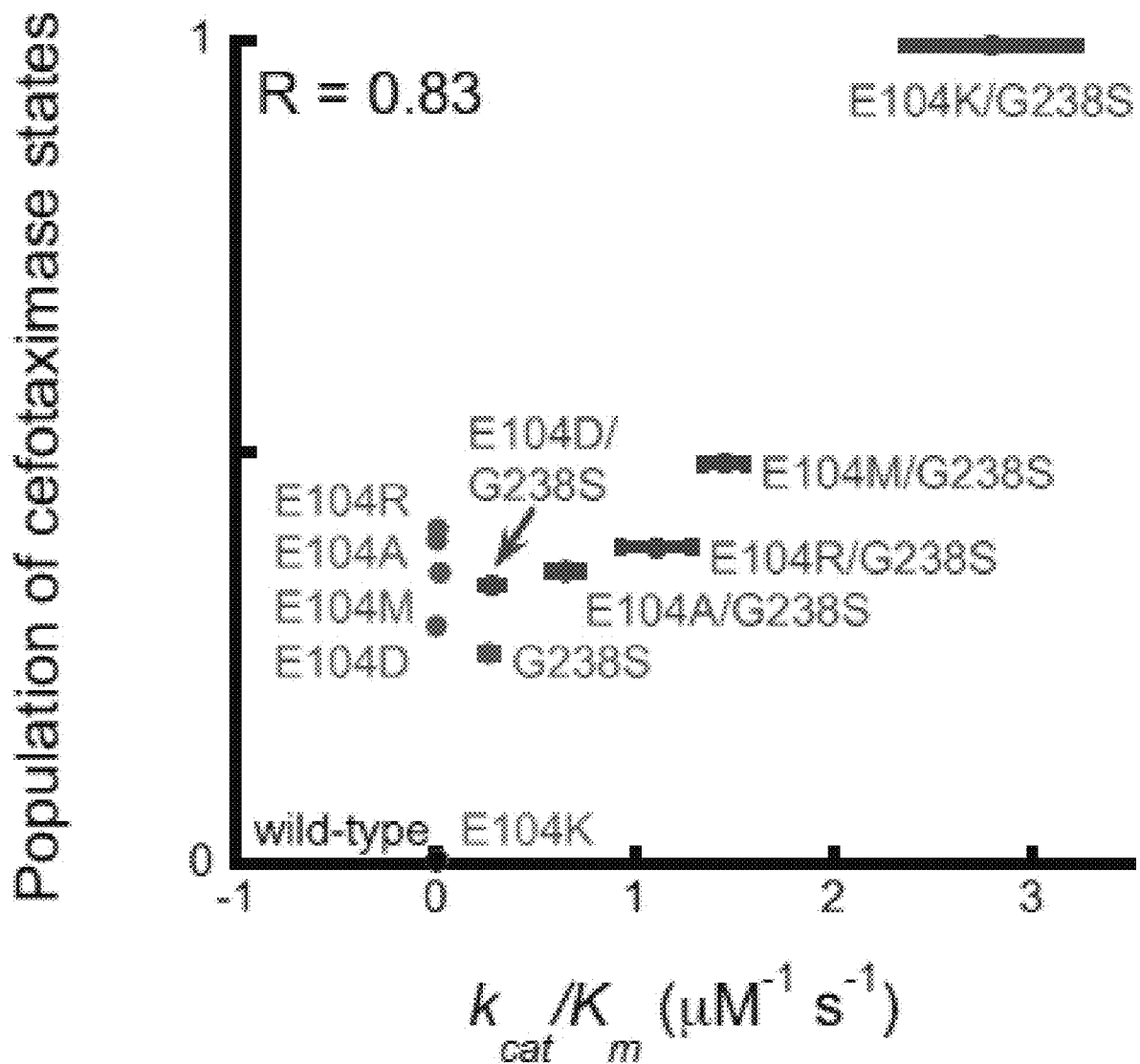
Figure 4D:
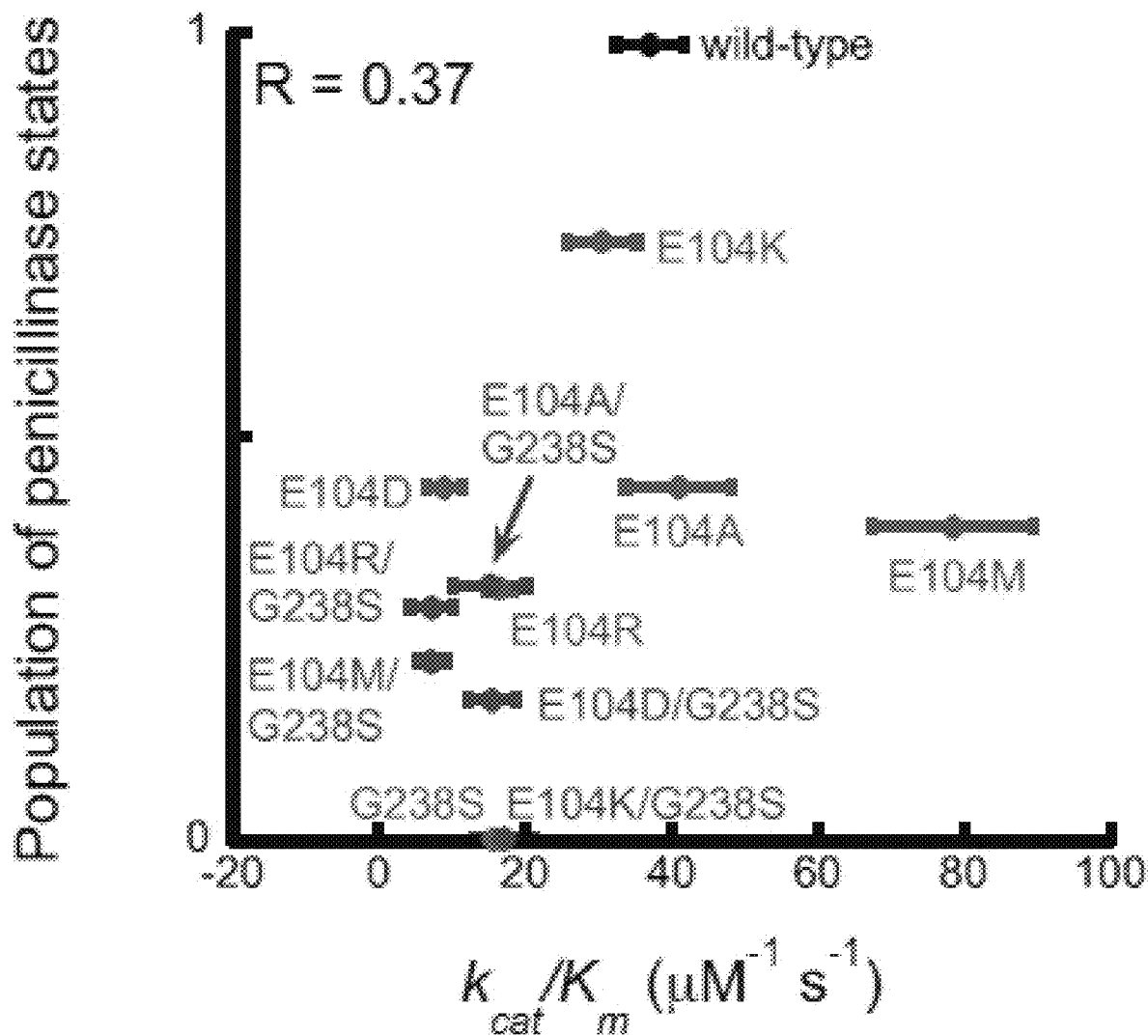
Figure 4E:
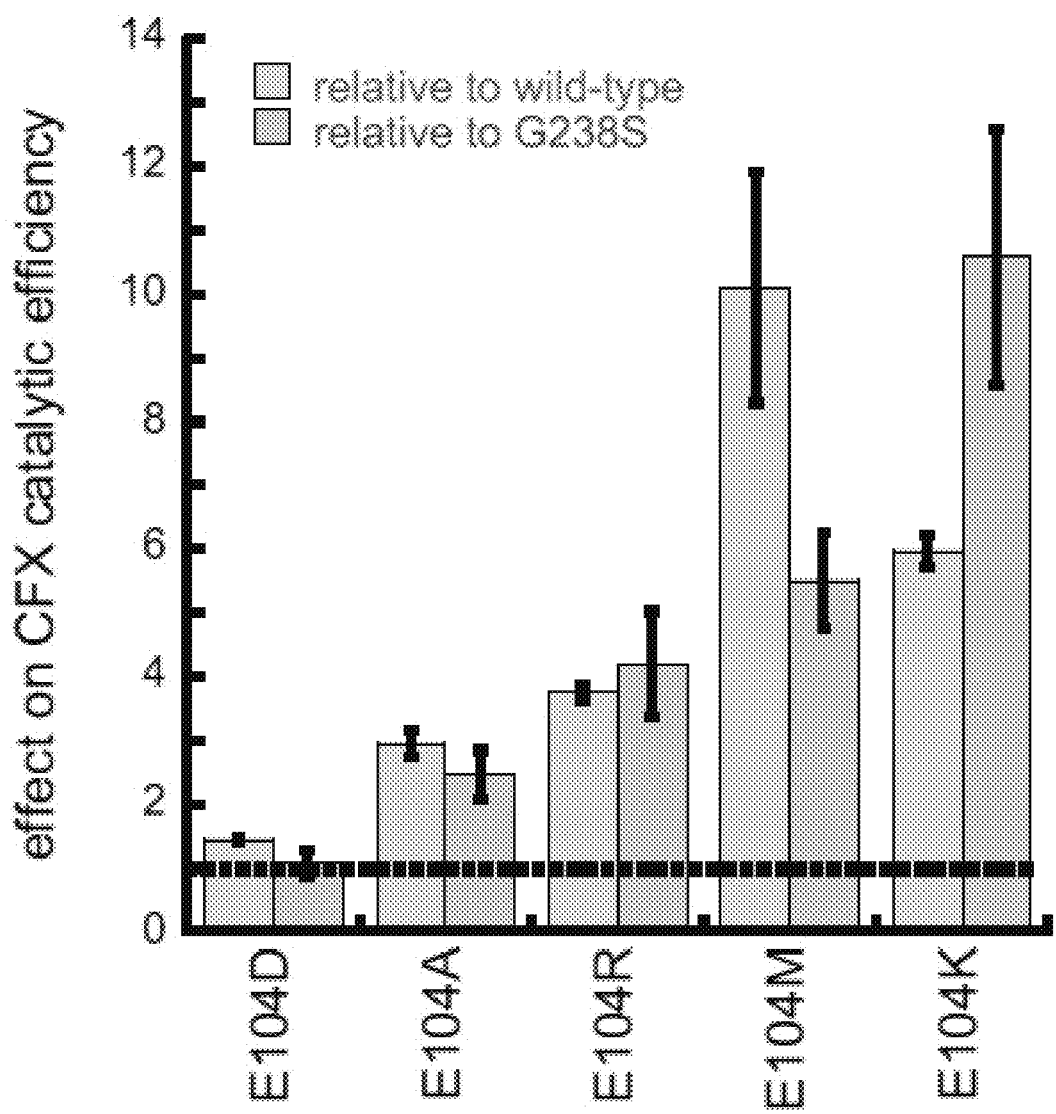
Figure 4F:
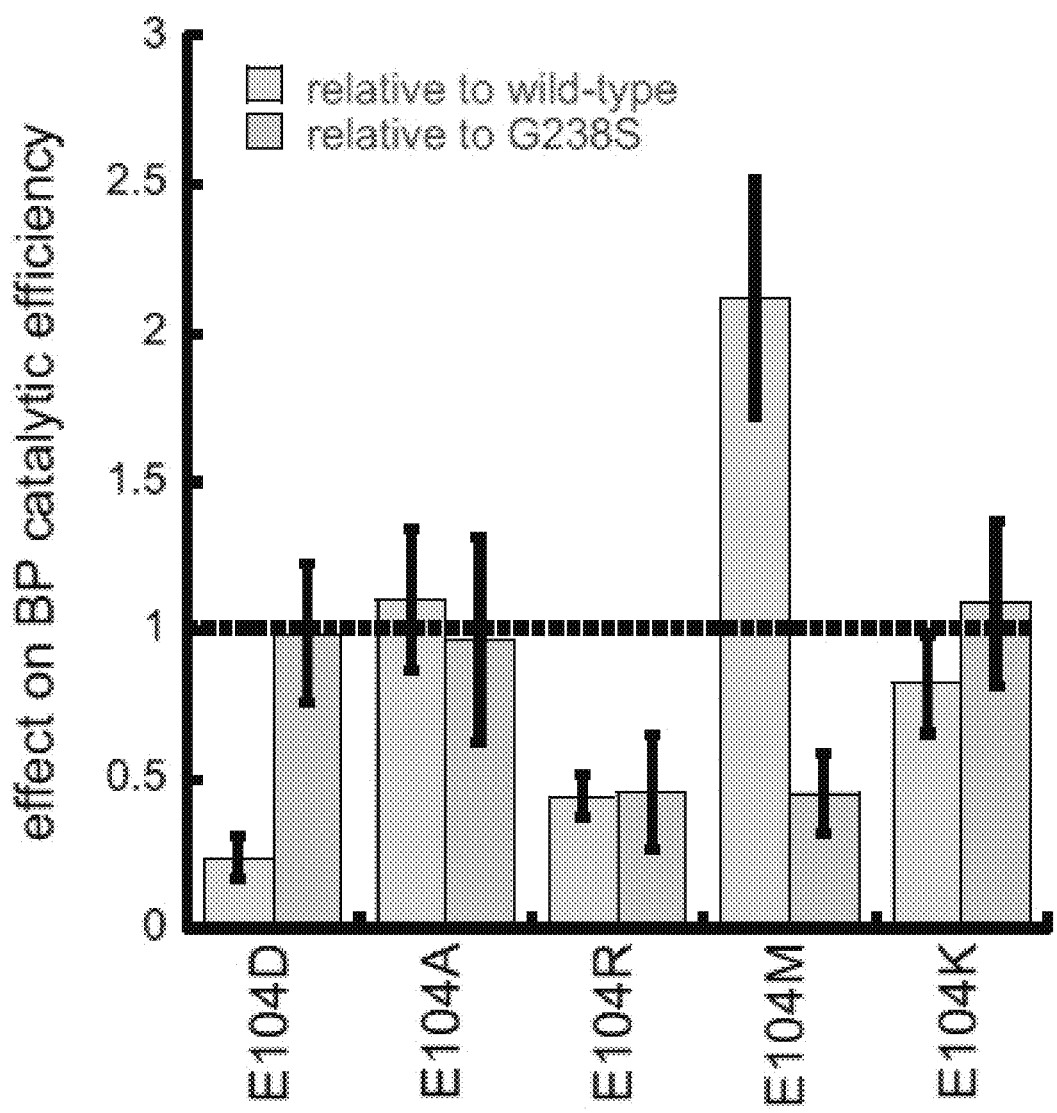
Figure 5A:
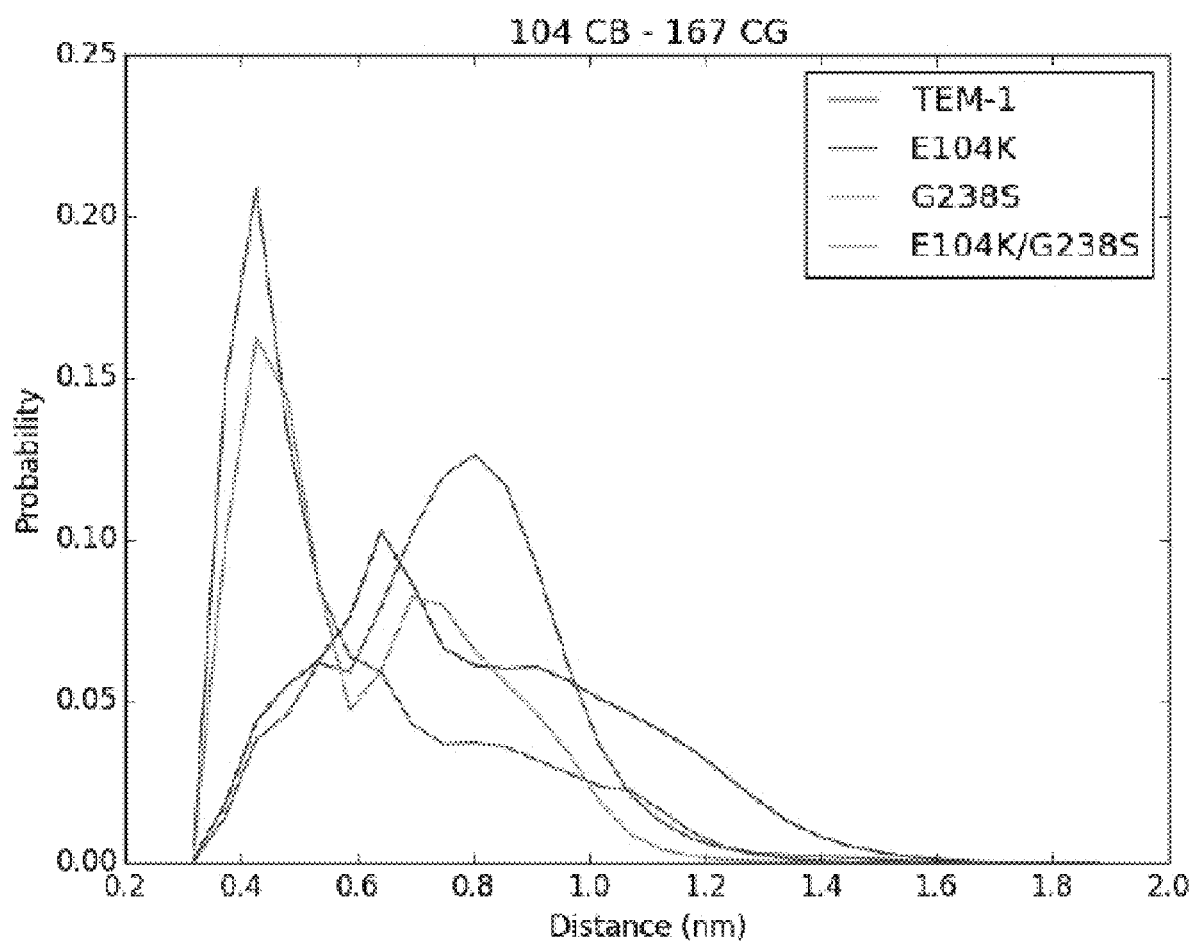
FIG. 5A and FIG. 5B depict a graph and ribbon diagram showing G238S and E104K substitutions restrict motion in the Ω-loop.
Figure 5B:

If the conformational preferences and amplitudes of the Ω-loop's fluctuations are the key determinant of the different specificities, then it was reasoned that the activities of other variants based on their 0-loops should be predictable. Since the single G238S substitution confers substantial resistance to cefotaxime but the E104K substitution does not, G238S was expected to resemble E104K/G238S and E104K was expected to more closely resemble wild-type. To test this hypothesis, MSMs for the single variants were constructed. The set of states preferred by the double mutant over the wild-type sequence (cefotaximase states) and those preferred by wild-type over the double mutant (penicillinase states) were then identified. Consistent with the hypothesis, the G238S substitution populates the cefotaximase states more than wild-type and E104K but less than E104K/G238S (FIG. 3B). E104K populates the penicillinase states more than G238S and E104K/G238S but less than wild-type (FIG. 4D). Examining the distribution of structures suggests that each substitution pins down the side of the Ω-loop to which it is adjacent. G238S appears to do this by hydrogen-bonding with the carbonyl of Asn170 in 70% of the population (FIG. 5B), an interaction that is absent in crystal structures. E104K increases interactions with the Ω-loop, as shown by a decreased distance between position 104 and Pro167 relative to wild-type (FIG. 5A). Interestingly, while the charge change has previously been cited as the basis for rate enhancement, these observations suggest van der Waals contacts with the Ω-loop may also play a role in increasing cefotaximase activity. Pinning down both sides of the Ω-loop leads to the large reduction in Ω-loop heterogeneity in the double mutant.

To definitively test the importance of Ω-loop heterogeneity, new variants designed to similarly restrict the Ω-loop rearrangements were made and cefotaximase activity was measured. If the electrostatic interactions between residue 104 and the Ω-loop are a key determinant of the populations of the Ω-loop's hidden states, then it was reasoned E104D should mimic wild-type, while E104R should more closely resemble E014K. The contribution of hydrophobic surface area was also tested by substituting aliphatic residues at position 104, it was predicted that longer side chains would form stronger interactions with the Ω-loop and generate greater cefotaximase activity. In isolation substitutions at position 104 have only a modest effect on activity, so all variants in combination with G238S were also tested to better assess their impact.

Figure 3C:
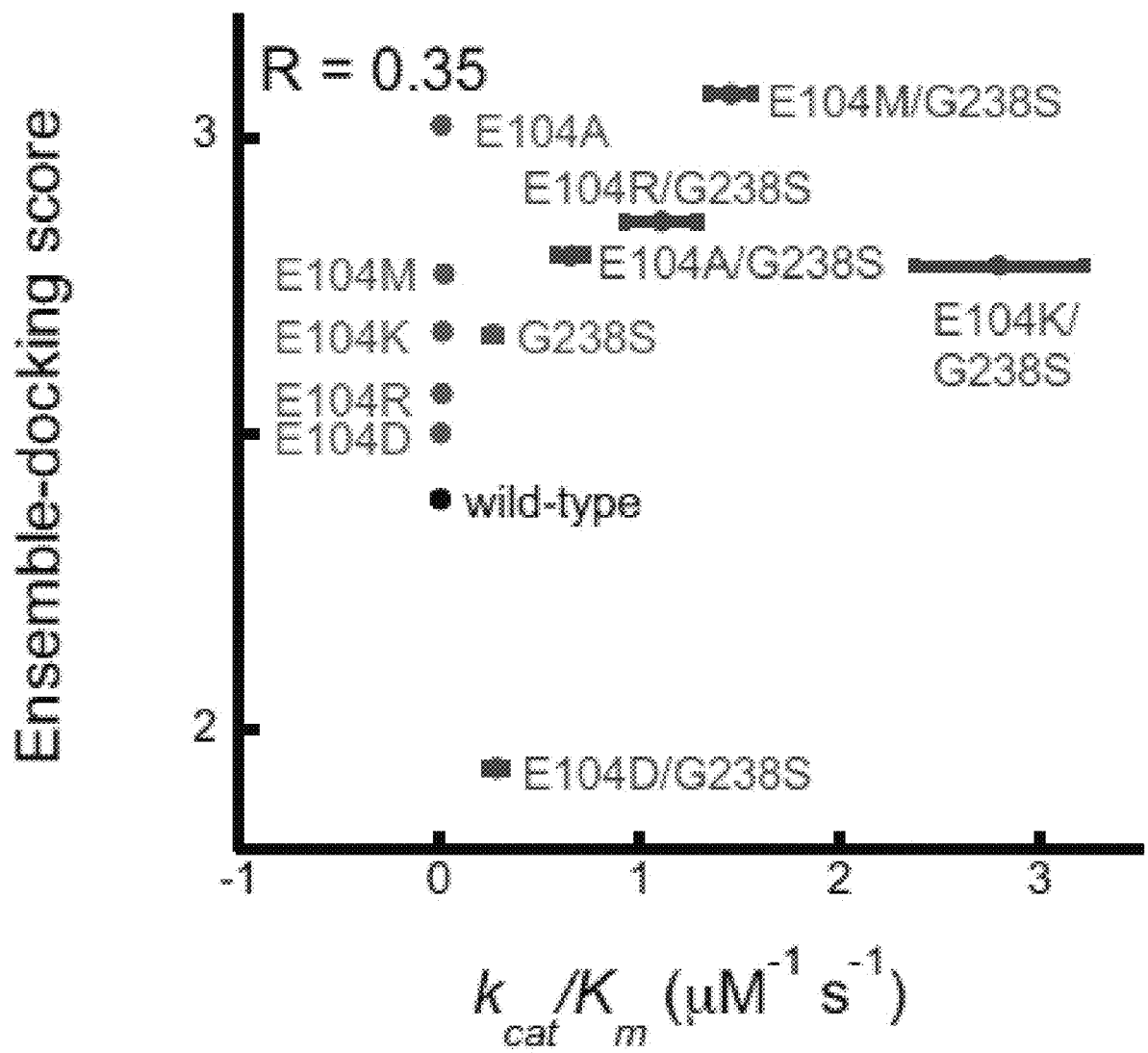
Figure 3D:
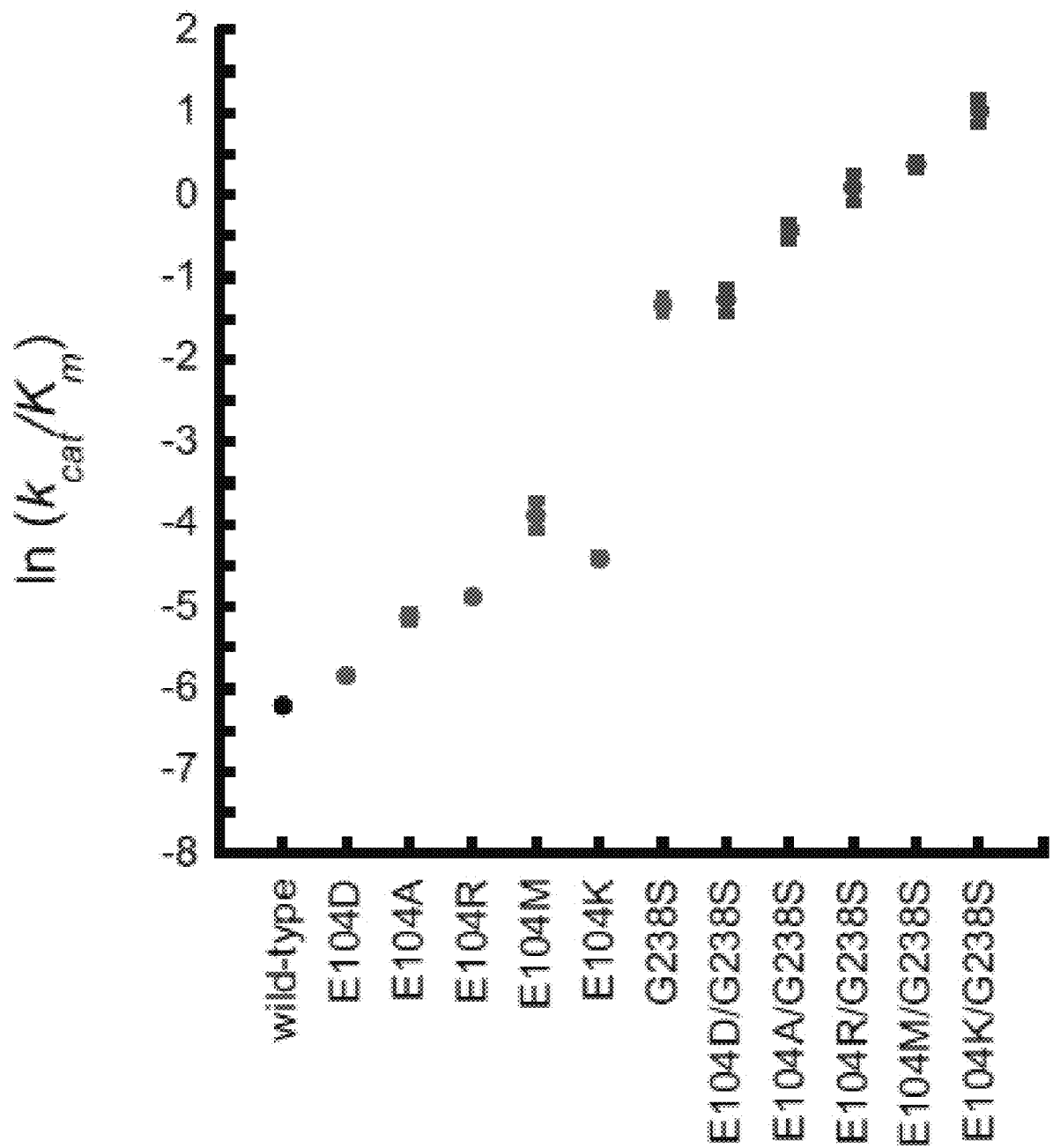

To test these designs, MSMs were first constructed and then the degree to which they populate the cefotaximase states was assessed. Their in vitro activities against cefotaxime and the extent to which they confer cefotaxime resistance to two laboratory strains of E. coli was then experimentally measured (Table 1 and Table 2). Similar trends exist in the single and double mutants, so focus was on the variants containing the sensitizing G238S mutation. As predicted, E104D/G238S has the same probability of adopting cefotaximase states as G238S alone and had similar activity against cefotaxime. In contrast with expectations based on charge arguments, E104R/G238S does not populate cefotaximase states as extensively as E104K/G238S (FIG. 3B). Furthermore, the reduced populations of these states are reflected in both in vitro and in vivo experiments (FIG. 3D and FIG. 4A). Comparing the conformations adopted by E104R/G238S to E104K/G238S reveals that the arginine interacts more strongly with residues 170 and 171 in the Ω-loop, displacing key interactions with the catalytic tural states, weighting each state by its equilibrium probability. Boltzmann docking of cefotaxime against each of the variants correlates well with these experiments (FIG. 3C) and represents a vast improvement over docking against single structures (R=0.35 versus R=0.07). The fact that this MSM model better predicts experimental data than Boltzman docking (R=0.83 versus R=0.35) could be interpreted as evidence for imperfections in the small molecule force field. However, future efforts to account for how protein-ligand interactions redistribute the equilibrium populations of different structures could lead to dramatic improvements without requiring any alteration of the underlying force field.

These results demonstrate that accounting for proteins' hidden states dramatically improves the predictive power of molecular modeling with common force fields, which are often blamed for any shortcoming in docking and molecular simulation studies. It is anticipated that Boltzmann docking will be valuable for predicting resistance to new compounds, especially when resistant variants have not yet been identified. Moreover, the tools developed here should be of great utility for other drug and protein design applications.

TABLE 1

MICs for E. coli strains expressing TEM β-lactamase variants*.

| | E. coli B strain | | | E. coli K-12 strain | | |
|---|---|---|---|---|---|---|
| | BP (mM) | CFX (μM) | Gentamicin (μM) | BP (mM) | CFX (μM) | Gentamicin (μM) |
| No plasmid | <0.023 | <0.035 | 0.68 | 0.05 | <0.035 | 0.34 |
| TEM-1 | 24.00 | <0.035 | 0.68 | 24.00 | <0.035 | 0.17 |
| G238S | 6.00 | 2.25 | 0.68 | 12.00 | 1.13 | 0.17 |
| E104K | 24.00 | <0.035 | 0.68 | 24.00 | 0.07 | 0.17 |
| E104K/G238S | 6.00 | 36.00 | 0.68 | 12.00 | 18.00 | 0.17 |
| E104R | 24.00 | <0.035 | 0.68 | 24.00 | 0.07 | 0.34 |
| E104R/G238S | 6.00 | 18.00 | 0.68 | 12.00 | 4.50 | 0.17 |
| E104A | 24.00 | <0.035 | 0.68 | 24.00 | <0.035 | 0.17 |
| E104A/G238S | 6.00 | 4.50 | 0.68 | 6.00 | 2.25 | 0.17 |
| E104D | 24.00 | <0.035 | 0.68 | 24.00 | <0.035 | 0.17 |
| E104D/G238S | 6.00 | 1.13 | 0.68 | 6.00 | 0.56 | 0.17 |
| E104M | 24.00 | <0.035 | 0.68 | 24.00 | 0.07 | 0.34 |
| E104M/G238S | 6.00 | 18.00 | 0.68 | 12.00 | 9.00 | 0.17 |
| E240K/E104K | 24.00 | <0.035 | 1.36 | 24.00 | <0.035 | 0.17 |
| R164E/G238S | 0.09 | <0.035 | 0.68 | 0.19 | <0.035 | 0.17 |
| R164D/G238S | 0.75 | <0.035 | 0.68 | 1.50 | <0.035 | 0.34 |

Figure 6:
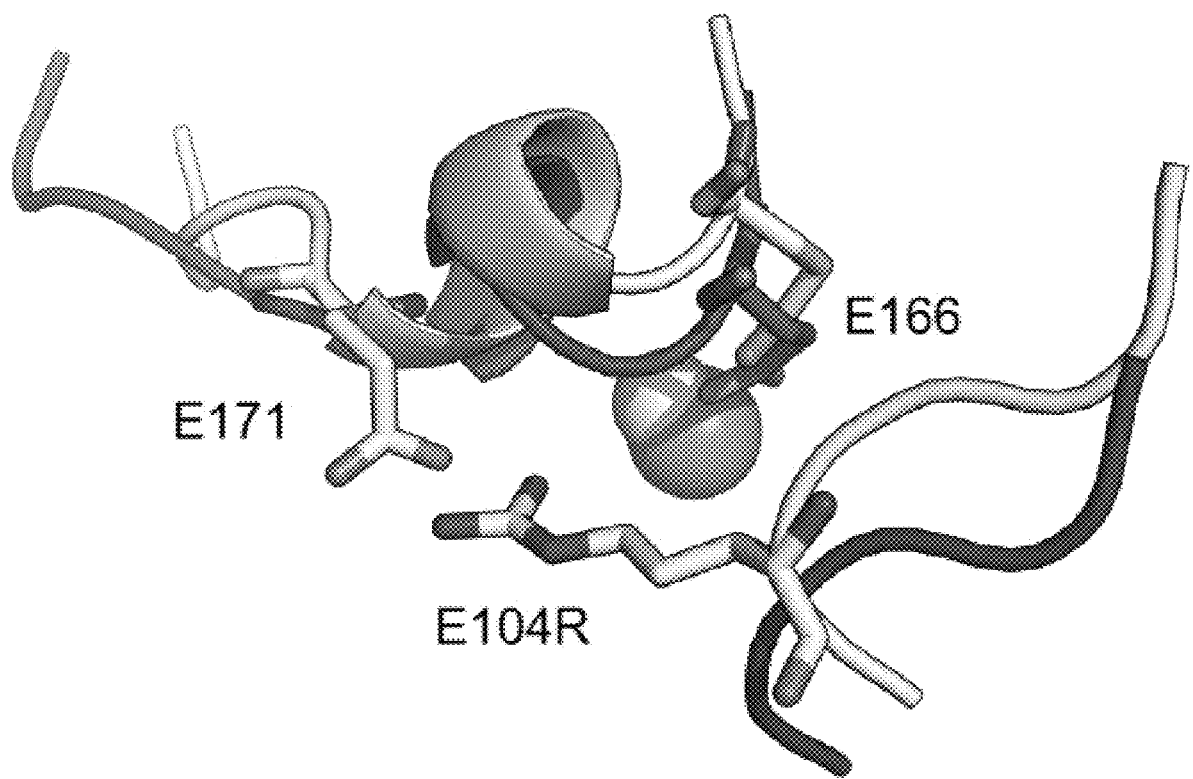
FIG. 6 depicts a ribbon diagram of one representative structure from the E104R/G238S variant (cyan) shows a salt-bridge between R104 and E171 in the Ω-loop. This causes displacement of the loop relative to wild-type (blue), altering the position of a key residue (E166) that is important for coordinating a catalytic water in the active site. It is hypothesized that this non-productive conformation accounts for E104R/G238S's lower activity ($k_{cat}$) against all substrates, particularly relative to E104K/G238S and E104M/G238S.

*MIC determination was repeated at least three times. Values are most commonly observed concentration with an error of +/− one well.

water in the active site and reducing activity against both benzylpenicillin and cefotaxime (FIG. 6). Consistent with the hypothesis that van der Waals interactions play an important role in pinning position 104 to the Ω-loop, E104M confers greater cefotaximase activity than E104A. In fact, in the wild-type background E104M has greater activity than either of the positively charged variants. Positive epistasis between G238S and E104K, however, results in this double mutant surpassing all others in cefotaximase efficiency. Taken together, these variants imply that both charge and hydrophobic surface area contribute to rate enhancement.

While these entirely protein-centric MSMs are capable of predicting new forms of resistance that mimic known variants, they are not capable of predicting how resistance will arise to new drugs. It was reasoned that it should be possible to make such predictions by docking small molecules against these structural ensembles. To test this hypothesis, a technique was developed called Boltzmann docking that approximates compounds' relative binding affinities by calculating the ensemble-average score across all of the struc- In addition to the variants discussed above, E240K/E104K, R164E/G238S and R164D/G238S were simulated and experimentally tested. Based on the importance of electrostatic interactions, it was predicted that these substitutions might pin the Ω-loop against the loops containing residues G238S and E104 in a manner analogous to what was observed for E104K/G238S and the other double mutants with cefotaximase activity. For E240K/E104K, it was hypothesized that replacing the negative charge at position 240 with a positive charge might relieve unfavorable long-distance charge interactions with the Ω-loop. However, simulations and MIC measurements show that this variant does not populate cefotaximase states and has no measurable resistance to cefotaxime. Position 164 resides on the opposite of the Ω-loop relative to the active site. For R164E/G238S and R164D/G238S, it was hypothesized hypothesized that replacing the positive charge with a negative charge would create unfavorable long-distance charge interactions with the Ω-loop and push it the opposite direction toward positions 104 and 238. Again, simulations and MIC measurements revealed that this design strategy was ineffective. Thus, biochemical intuition based on crystal structures proved inferior to simulation and machine learning in predicting the outcome of several different design strategies.

TABLE 2

Michaelis-Menten parameters for TEM β-lactamase variants^.

| | benzylpenicillin | | | cefotaxime | | |
|---|---|---|---|---|---|---|
| | $k_{cat}$ (s$^{-1}$) | $K_m$ (μM) | $k_{cat}/K_m$ (μM/s) | $k_{cat}$ (s$^{-1}$) | $K_m$ (μM) | $k_{cat}/K_m$ (μM/s) |
| TEM-1 | 1300 ± 50 | 35 ± 4 | 37 ± 5 | ND* | ND* | $2.0 \times 10^{-3} \pm 0.5 \times 10^{-4}$ |
| G238S | 66 ± 1 | 4.3 ± 0.4 | 16 ± 2 | 50 ± 3 | 190 ± 20 | 0.26 ± 0.03 |
| E104K | 1200 ± 60 | 39 ± 6 | 30 ± 5 | ND* | ND* | $1.2 \times 10^{-2} \pm 0.4 \times 10^3$ |
| E104K/G238S | 38 ± 2 | 2.3 ± 0.5 | 17 ± 4 | 87 ± 4 | 31 ± 5 | 2.8 ± 0.4 |
| E104R | 970 ± 40 | 60 ± 6 | 16 ± 2 | ND* | ND* | $7.6 \times 10^{-3} \pm 0.1 \times 10^{-4}$ |
| E104R/G238S | 25 ± 2 | 3.6 ± 1.4 | 7.1 ± 2.9 | 38 ± 2 | 34 ± 5 | 1.1 ± 0.2 |
| E014A | 1200 ± 70 | 30 ± 5 | 41 ± 7 | ND* | ND* | $6.0 \times 10^{-3} \pm 0.4 \times 10^{-3}$ |
| E104A/G238S | 52 ± 4 | 3.5 ± 1.1 | 15 ± 5 | 47 ± 2 | 72 ± 7 | 0.65 ± 0.07 |
| E104D | 1700 ± 200 | 190 ± 40 | 8.8 ± 2.4 | ND* | ND* | $2.9 \times 10^{-3} \pm 0.5 \times 10^{-4}$ |
| E104D/G238S | 45 ± 1 | 2.9 ± 0.6 | 15 ± 3 | 57 ± 5 | 200 ± 30 | 0.28 ± 0.04 |
| E104M | 1100 ± 40 | 14 ± 2 | 78 ± 11 | 4.8 ± 0.5 | 230 ± 30 | $2.1 \times 10^{-2} \pm 0.4 \times 10^{-2}$ |
| E104M/G238S | 110 ± 8 | 15 ± 4 | 7.1 ± 1.9 | 78 ± 2 | 53 ± 4 | 1.5 ± 0.1 |

^Standard error values from the fits are reported.
*Michaelis-Menten curve did not saturate. $k_{cat}/K_m$ was determined by a linear fit.

Methods for Example 1

Molecular Dynamics Simulations.

Five 500 ns simulations were run for each variant with Gromacs 4.6.5 (Van Der Spoel et al. *J Comput Chem* 2005; 26: 1701-1718) and the Amber03 force field using previously reported settings (Bowman et al. *PNAS* 2015; 112: 2734-2739 and Bowman et al. *PNAS* 2012; 109: 11681-11686), which are reviewed below. Modeller (Webb and Sali. *Curr Protoc Bioinformatics* 2014; 47: 5.6.1-5.6.32) was used to create a homology model of each variant based on PDB 1BTL (Jelsch et al. *Proteins* 1993; 16: 364-383) that was then used as the starting point for simulations. Each of these starting structures was solvated with TIP3P water in a dodecahedron box that extended one nm beyond the protein in any dimension and sodium ions were added to neutralize the charge. This system was energy minimized with the steepest descent algorithm until the maximum force fell below 1,000 kJ/mol/min using a step size of 0.01 nm and a cut-off distance of 1.2 nm for the neighbor list, Coulomb interactions, and Van der Waals interactions. The solvent was then equilibrated in a one ns simulation with a position restraint on all protein heavy atoms. All bonds were constrained with the LINCS algorithm and virtual sites were used to allow a 4 fs time step. Cut-offs of 1.1 nm, 0.9 nm, and 0.9 nm were used for the neighbor list, Coulomb interactions, and Van der Waals interactions, respectively. The Verlet cut-off scheme was used for the neighbor list and particle mesh Ewald was employed for the electrostatics. The v-rescale thermostat was used to hold the temperature at 300 K and the Berendsen barostat was used to bring the system to 1 bar pressure. For the production runs, the position restraint was removed and the Parrinello-Rahman barostat was employed. Structures were drawn with PyMOL.

MSM Construction and Analysis.

Figure 7:
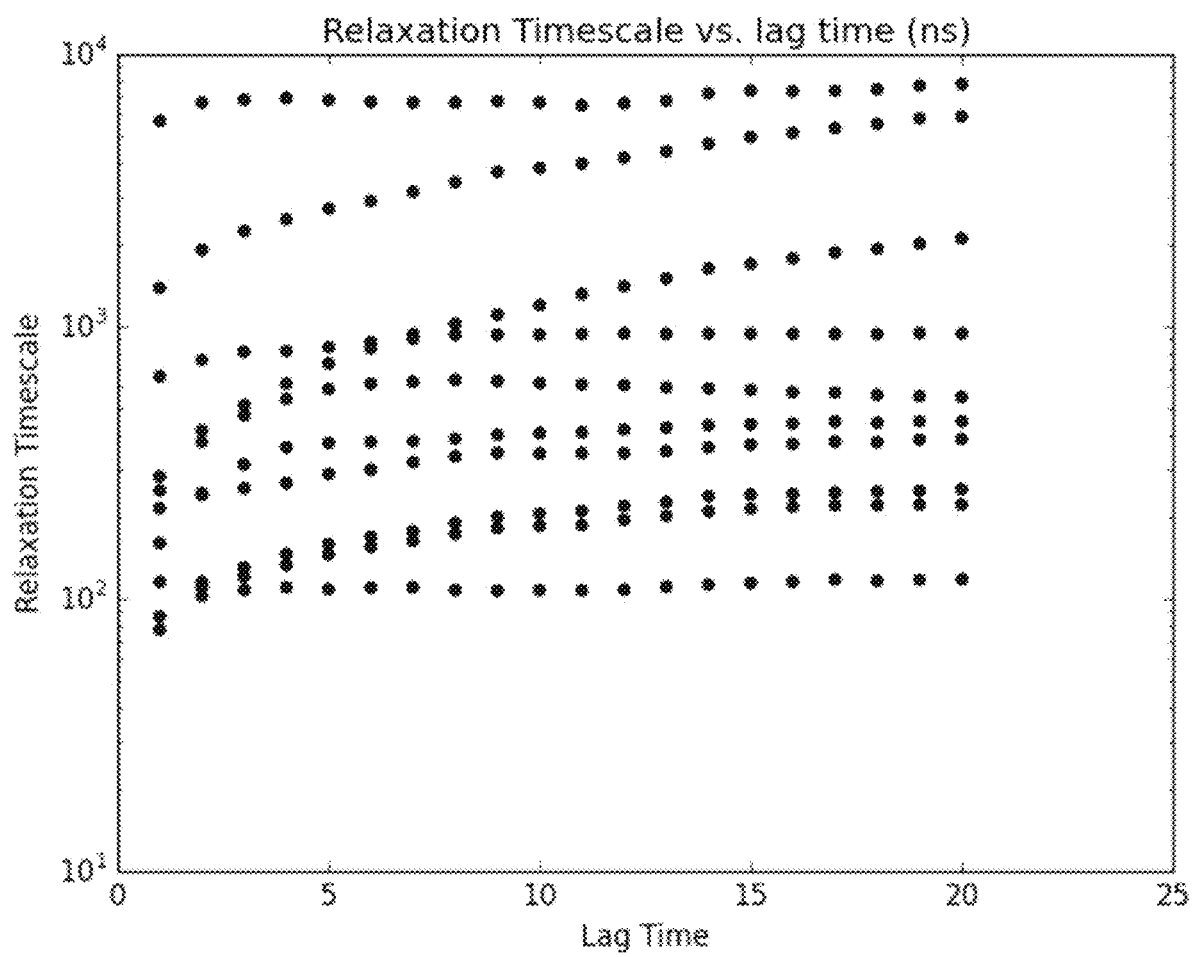

Markov state models (MSMs) were constructed with MSMBuilder (Bowman et al. *Methods* 2009; 49: 197-201). MSMs for individual variants that were used for ensemble-docking were created by clustering the data with a k-centers algorithm based on the RMSD between heavy atoms in residues surrounding the active site (residues 69-73, 103, 105, 130-132, 165-173, 216, 234-237, and 244) until every cluster had a radius—i.e. maximum distance between any data point in the cluster and the cluster center—less than 1.0 Å. Then, three sweeps of a k-medoids update step were used to center the clusters on the densest regions of conformational space. FIG. 7 shows these models satisfy the Markov assumption for lag times as small as 1 ns. Based on past work demonstrating that thermodynamics converge far more quickly than kinetics (Huang et al. *PNAS* 2009; 106: 19765-19769), equilibrium populations of each state were determined by calculating a matrix of transition probabilities between every pair of states with the transpose method and a lag time of 10 ps and solving for the normalized left-eigenvector of this matrix.

MSMs for comparing the structural preferences of different variants were constructed based on the same set of active site residues. First, every 100th data point from simulations of each variant were pooled together and clustered into 1,000 states with a k-medoids algorithm. Then the equilibrium probability of each state for a given variants was calculated using the same approach described before using just the data for that variant. Using a common set of states to describe the thermodynamics and kinetics of each variant provides a basis for directly comparing the probabilities that different variants will adopt a given conformation.

Inter-atomic distances were calculated with MDTraj (McGibbon et al. *Biophysical Journal* 2015; 109: 1529-1532). Two atoms were assumed to be in contact with one another if their centers were within 4 Å. The probability of a contact was calculated by identifying all the states where a pair of residues are in contact and then summing up the equilibrium populations of these states.

Docking. Docking against individual structures was performed with Surflex-dock (Jain. *J Comput Aided Mol Des* 2007; 21: 281-306). The structures of benzylpenicillin and cefotaxime were generated using the Concord module of SYBYL-X 2.1.1 and minimized using the Tripos force field. Surflex-Dock receptor protomols were generated with a threshold of 0.5 and a bloat of 3.0. These protomols were then used to screen various ligands for receptor complementarity. The Hammerhead scoring function inherent to Surflex was used to score the resulting poses. The default '-pgeom' docking accuracy parameter set was implemented.

Ensemble-docking was generated using the same settings to dock the substrates against the cluster centers from each state of the MSMs built for an individual variant. The final score was then calculated as the weighted-average of the scores for each state, using the equilibrium probabilities of each state as their weights.

Protein Expression and Purification.

TEM-1 was subcloned using NdeI and XhoI restriction sites into the multiple cloning site of a pET24 vector (Life Technologies), and its native export signal sequence was replaced by the OmpA signal sequence to maximize export efficiency. Site-specific variants were constructed via site-directed mutagenesis and verified by DNA sequencing. Plasmids were then transformed into BL21(DE3) Gold cells (Agilent Technologies) for expression under T7 promoter control.

Cells were induced with 1 mM IPTG at OD=0.6 and grown at 18° C. for 15 hours before harvesting. β-lactamases were isolated from the periplasmic fraction using osmotic shock lysis: Cells were resuspended in 30 mM Tris pH 8, 20% sucrose and stirred for 10 minutes at room temperature. After centrifugation, the pellet was resuspended in ice-cold 5 mM $MgSO_4$ and stirred for 10 minutes at 4° C. After centrifugation, the supernatant was dialyzed against 20 mM sodium acetate, pH=5.5 and purified using cation exchange chromatography (BioRad UNOsphere Rapid S column) followed size exclusion chromatography (BioRad ENrich SEC 70 column) into storage buffer (20 mM Tris, pH=8.0).

Activity Measurements.

Enzyme activities against BP and CFX substrates were measured in 50 mM potassium phosphate, 10% glycerol (v:v) pH=7.0 at 25° C. using 2 nM or 10 nM enzyme. The reaction was monitored at 232 nm ($\varepsilon_{BP}$=-1096 $M^{-1}$ $cm^{-1}$) or 265 ($\varepsilon_{CFX}$=-6643 $M^{-1}$ $cm^{-1}$) using a Cary 100 UV-vis spectrophotometer (Agilent Technologies). Velocities were plotted as a function of substrate concentration and fit by the Michaelis-Menten equation to extract $k_{cat}$ and $K_m$ values. Enzymes that did not exhibit saturation behavior under the tested conditions were fit by a line, and the slopes are reported as $k_{cat}/K_m$.

Minimal Inhibitory Concentration (MIC) Measurements.

Site-specific variants of TEM-1 were constructed via site-directed mutagenesis of the pBR322 plasmid and verified by DNA sequencing. Plasmids were then transformed into BL21(DE3) cells (Intact Genomics) and DH5a cells (Life Technologies) to create strains in which β-lactamases are expressed using a native promoter.

Antibiotic resistance of the strains was determined by measuring their minimum inhibitory concentrations (MIC90's) using the broth microdilution method according to the Clinical and Laboratory Standards Institute (CLSI, formerly the NCCLS) guidelines (CLSI document M07-A9, 2012). Each well of a 96-well microtiter plate was filled with 75 μL of sterile Mueller Hinton II (MHII) media broth (Sigma). Each antibiotic was dissolved in water making a 20 mM solution, then diluted with sterile MHII media broth to 192 mM (BP) or 288 μM (CFX). Exactly 75 μL of the compound solution was added to the first well of the microtiter plate and 2-fold serial dilutions were made down each row of the plate. Exactly 75 μL of bacterial inoculum ($5 \times 10^5$ CFU/mL) was then added to each well giving a total volume of 150 μL/well and compound concentration gradients of 48 mM-23 μM (BP) and 72 μM-0.04 μM (CXF). The plate was incubated at 37° C. for 17 h, and then each well was examined for bacterial growth. The MIC90 was recorded as the lowest compound concentration required to inhibit 90% of bacterial growth as judged by turbidity of the culture media relative to a row of wells filled with a water standard. Gentamicin was included in a control row at a concentration gradient of 174 μM-0.09 μM.

REFERENCES FOR EXAMPLE 1

1. World Health Organization. *Antimicrobial resistance: global report on surveillance*. (World Health Organization, 2014).
2. Bush, K. & Jacoby, G. A. Updated functional classification of beta-lactamases. *Antimicrob. Agents Chemother.* 54, 969-976 (2010).
3. Salverda, M. L. M., de Visser, J. A. G. M. & Barlow, M. Natural evolution of TEM-1 13-lactamase: experimental reconstruction and clinical relevance. *FEMS Microbiol. Rev.* 34, 1015-1036 (2010).
4. Bowman, G. R. An overview and practical guide to building Markov state models. *Adv. Exp. Med. Biol.* 797, 7-22 (2014).
5. Savard, P.-Y. & Gagné, S. M. Backbone Dynamics of TEM-1 Determined by NMR: Evidence for a Highly Ordered Protein †. *Biochemistry* 45, 11414-11424 (2006).
6. Orencia, M. C., Yoon, J. S., Ness, J. E., Stemmer, W. P. & Stevens, R. C. Predicting the emergence of antibiotic resistance by directed evolution and structural analysis. *Nat. Struct. Biol.* 8, 238-242 (2001).
7. Jelsch, C., Mourey, L., Masson, J. M. & Samama, J. P. Crystal structure of *Escherichia coli* TEM1 beta-lactamase at 1.8 A resolution. *Proteins* 16, 364-383 (1993).
8. Zaccolo, M. & Gherardi, E. The effect of high-frequency random mutagenesis on in vitro protein evolution: a study on TEM-1 beta-lactamase. *J. Mol. Biol.* 285, 775-783 (1999).
9. Dellus-Gur, E. et al. Negative Epistasis and Evolvability in TEM-1 13-Lactamase—The Thin Line between an Enzyme's Conformational Freedom and Disorder. *J. Mol. Biol.* 427, 2396-2409 (2015).
10. Bowman, G. R., Bolin, E. R., Hart, K. M., Maguire, B. C. & Marqusee, S. Discovery of multiple hidden allosteric sites by combining Markov state models and experiments. *Proc. Natl. Acad. Sci. U.S.A.* 112, 2734-2739 (2015).
11. Bowman, G. R. & Geissler, P. L. Equilibrium fluctuations of a single folded protein reveal a multitude of potential cryptic sites. *Proc. Natl. Acad. Sci. U.S.A.* 109, 11681-11686 (2012).
12. Zou, T., Risso, V. A., Gavira, J. A., Sanchez-Ruiz, J. M. & Ozkan, S. B. Evolution of conformational dynamics determines the conversion of a promiscuous generalist into a specialist enzyme. *Mol Biol Evol* 32, msu281-143 (2014).
13. Motlagh, H. N., Wrabl, J. O., Li, J. & Hilser, V. J. The ensemble nature of allostery. *Nature* 508, 331-339 (2014).
14. Kohlhoff, K. J. et al. Cloud-based simulations on Google Exacycle reveal ligand modulation of GPCR activation pathways. *Nat Chem* 6, 15-21 (2014).
15. Wand, A. J. The dark energy of proteins comes to light: conformational entropy and its role in protein function revealed by NMR relaxation. *Curr. Opin. Struct. Biol.* 23, 75-81 (2013).
16. Plattner, N. & Noe, F. Protein conformational plasticity and complex ligand-binding kinetics explored by atomistic simulations and Markov models. *Nat Commun* 6, 7653 (2015).

17. Boehr, D. D., McElheny, D., Dyson, H. J. & Wright, P. E. The dynamic energy landscape of dihydrofolate reductase catalysis. *Science* 313, 1638-1642 (2006).
18. Henzler-Wildman, K. & Kern, D. Dynamic personalities of proteins. *Nature* 450, 964-972 (2007).
19. Fraser, J. S. et al. Hidden alternative structures of proline isomerase essential for catalysis. *Nature* 462, 669-673 (2009).
20. Weinreich, D. M., Delaney, N. F., Depristo, M. A. & Hartl, D. L. Darwinian evolution can follow only very few mutational paths to fitter proteins. *Science* 312, 111-114 (2006).
21. Hall, B. G. Predicting evolution by in vitro evolution requires determining evolutionary pathways. *Antimicrob. Agents Chemother.* 46, 3035-3038 (2002).
22. Bowman, G. R., Huang, X. & Pande, V. S. Using generalized ensemble simulations and Markov state models to identify conformational states. *Methods* 49, 197-201 (2009).
23. Tokuriki, N. & Tawfik, D. S. Protein dynamism and evolvability. *Science* 324, 203-207 (2009).
24. Strynadka, N. C. et al. Molecular structure of the acyl-enzyme intermediate in beta-lactam hydrolysis at 1.7 A resolution. *Nature* 359, 700-705 (1992).
25. Van Der Spoel, D. et al. GROMACS: fast, flexible, and free. *J Comput Chem* 26, 1701-1718 (2005).
26. Webb, B. & Sali, A. Comparative Protein Structure Modeling Using MODELLER. *Curr Protoc Bioinformatics* 47, 5.6.1-5.6.32 (2014).
27. Huang, X., Bowman, G. R., Bacallado, S. & Pande, V. S. Rapid equilibrium sampling initiated from nonequilibrium data. *Proc. Natl. Acad. Sci. U.S.A.* 106, 19765-19769 (2009).
28. McGibbon, R. T. et al. MDTraj: A Modern Open Library for the Analysis of Molecular Dynamics Trajectories. *Biophysical Journal* 109, 1528-1532 (2015).
29. Jain, A. N. Surflex-Dock 2.1: robust performance from ligand energetic modeling, ring flexibility, and knowledge-based search. *J. Comput. Aided Mol. Des.* 21, 281-306 (2007).
30. National Committee for Clinical Laboratory Standards. *Methods for Dilution Antimicrobial Susceptibility Tests for Bacteria that Grow Aerobically.* (CLSI document M07-A9, 2012).

Example 2. Cryptic Sites and Rational Drug Design

Figure 8:
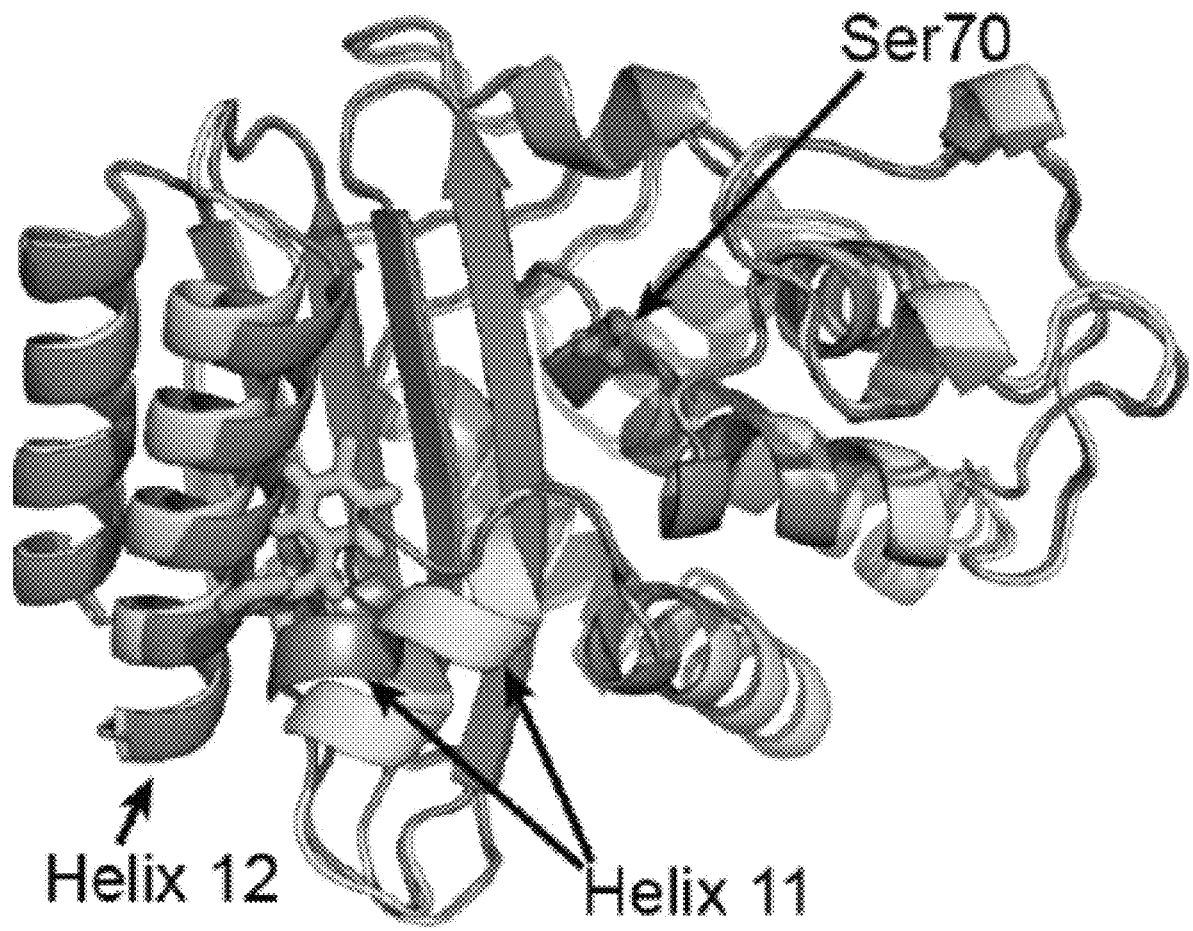
FIG. 8 depicts a ribbon diagram showing a cryptic site in TEM-1 β-lactamase. The inhibitor-bound structure (yellow) with inhibitor (cyan) is overlaid on the inhibitor-free structure (blue) highlighting a key catalytic serine (Ser70, magenta).

Cryptic sites are pockets that are not present in a protein's ligand-free crystal structure but open when the protein fluctuates away from its ground-state structure. They may exert allosteric control over the protein's activity or occur at key binding interfaces, providing a novel means to sterically block interactions with binding partners (e.g. small molecules or other proteins). For example, an effort to identify β-lactamase inhibitors revealed a compound that binds in a cryptic pocket that is not present in the ligand-free crystal structure and allosterically inhibits the enzyme despite being over 15 Å from the key catalytic serine (FIG. 8). The fact that all proteins adopt an ensemble of different structures—many of which have not been characterized—means that cryptic sites could be quite common and provide a wealth of new opportunities for controlling proteins' functions. They could provide a powerful means to target the large number of proteins that are currently considered undruggable because their crystal structures do not reveal pockets where drugs can bind tightly. They could also provide novel means to control conventional drug targets, such as β-lactamases.

Figure 9:
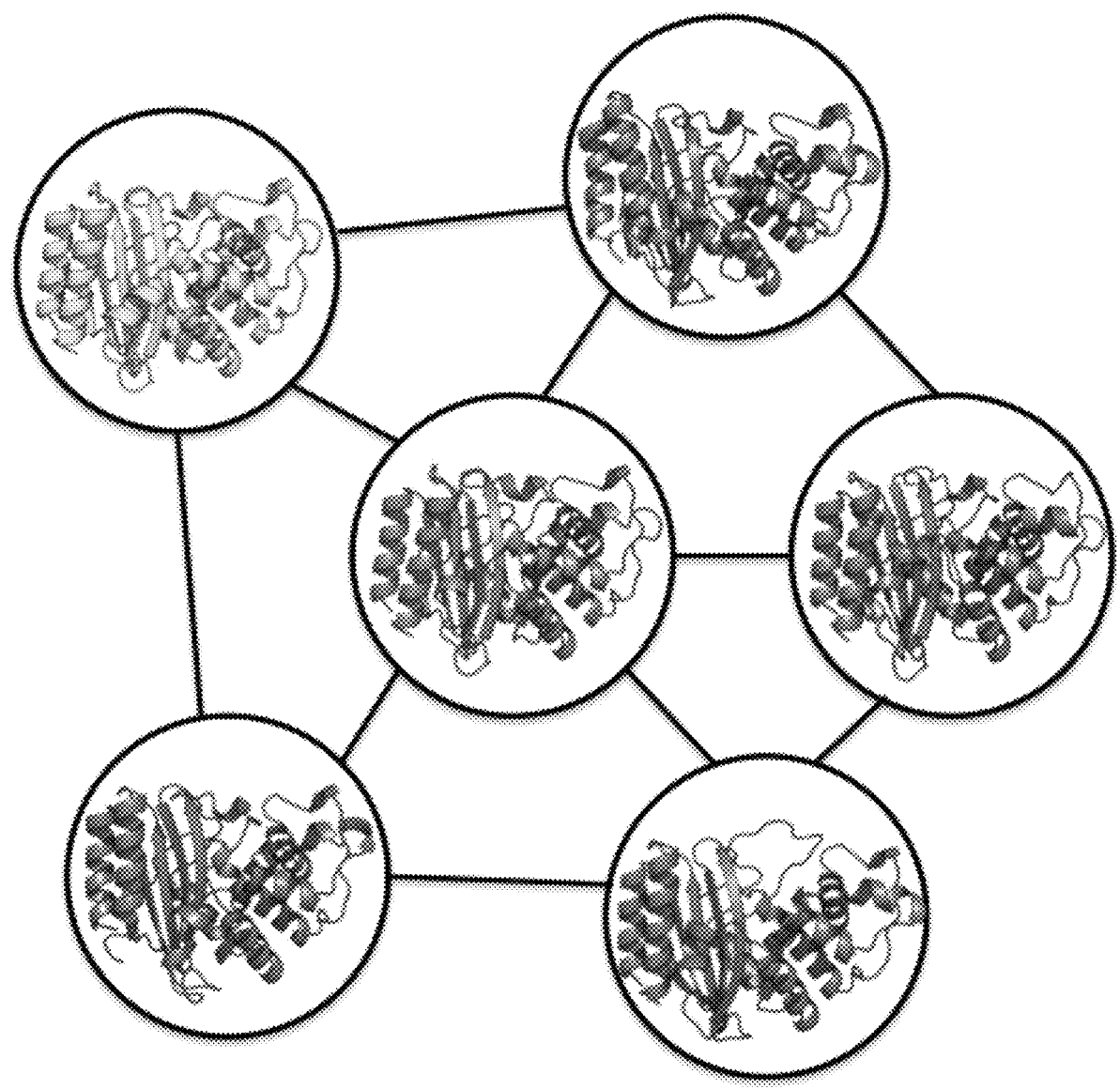
FIG. 9 depicts a representative subset of the states in our β-lactamase MSM showing that the drug free structure (blue), the allosteric ligand-bound structure (yellow) and a variety of other structures (gray) are captured.

The ability to map out the ensemble of structures a protein adopts with the atomistic detail required for rational drug design would provide a powerful means to identify cryptic sites and then design drugs that target them. Described herein are novel computational and experimental tools developed to achieve this goal. In particular, Markov state model (MSM) methods provide unprecedented access to the ensemble of different structures a protein adopts by integrating information from thousands of atomically-detailed molecular dynamics simulations to identify the structural states a protein tends to adopt, their equilibrium probabilities, and the rates of transitioning between them. This paradigm provides quantitative models of slow conformational changes even if no individual simulation encompasses the entire process of interest as long as one has sets of simulations that collectively capture all the small steps required along the way. FIG. 9 shows a representative subset of the 5K states in the model of β-lactamase. It is encouraging that this model discovers conformations like the known drug-bound conformation (yellow structure in both FIG. 8 and FIG. 9) given that all the simulations used to construct the model were started from the drug-free crystal structure (blue structure). The model also predicts a number of other cryptic sites that have never been observed before. To test these predictions, a thiol labeling technique was developed. For these experiments, a cysteine at a buried position was introduced that becomes exposed to solvent if a predicted pocket forms. The technique then exploits the reactivity of the cysteine's thiol group to assay whether the pocket opens and exposes the cysteine to solvent. Controls confirm that labeling is not simply due to protein unfolding. Measuring the activity of a fully labeled protein sample also provides a first test of whether a small molecule that binds in a cryptic pocket has the capacity to exert allosteric control over the protein. Using these techniques, two new cryptic sites in TEM-1 β-lactamase have been identified.

The work described herein explores the therapeutic potential of the cryptic sites identified in TEM-1 β-lactamase by discovering allosteric inhibitors and activators that bind these sites. The physical mechanisms underlying the formation and function of these sites will also be elucidated to lay a foundation for future efforts to target cryptic sites in other proteins.

This research provides a desperately needed means of developing new drugs to combat antibiotic-resistant infections and a deeper understanding of allosteric modulators that will facilitate future work on new proteins. The most immediate impact will be the discovery of novel lead compounds for inhibiting β-lactamase-mediated antibiotic resistance. Future drug development efforts could lead to combination therapies that use discovered inhibitors to restore the efficacy of existing antibiotics, thereby reducing the morbidity and financial burden of antibiotic-resistant infections. The ability to discover and manipulate allosteric sites will also have far reaching consequences. For example, targeting enzyme active sites limits drug design efforts to discovering inhibitors. However, allosteric sites could also be manipulated to upregulate desirable activities, providing a way to reverse the effects of deleterious mutations. Future discovery of cryptic sites in proteins that are currently considered undruggable would provide a powerful means to control these otherwise intractable targets.

Most recent drug discovery programs have used high-throughput screens and rational drug design. While both approaches have had noteworthy successes, they also have limitations that are particularly pertinent to the discovery of allosteric modulators. For example, high-throughput screening can rapidly search through large libraries of chemicals for efficacious lead compounds but it is common for these screens to fail because chemical space is too large to explore exhaustively. In particular, it is easy to imagine a library that doesn't contain chemicals that bind cryptic pockets and, therefore, never realizing these pockets exist. Rational drug design provides a more directed search by integrating information from crystallographic structures with the results of experimental tests of promising compounds to design small molecules that will bind tightly to specific sites. However, this strategy is limited by the information contained in the available crystal structures. For example, it would have been impossible to intentionally design the allosteric β-lactamase inhibitor in FIG. 8 prior to solving a structure with this pocket open. As a result, neither high-throughput screens nor rational design have revealed a wealth of cryptic sites but the possibility that they exist cannot be discounted.

Mounting evidence for conformational selection suggests the possibility of finding cryptic sites by monitoring a protein's equilibrium fluctuations even in the absence of an allosteric drug. The conformational selection mechanism posits that the different structures a protein adopts are all present at equilibrium and that small molecules shift this conformational ensemble by binding to and stabilizing particular structures. Unfortunately, it is still extremely difficult to map out the ensemble of structures a protein adopts with the atomistic detail required to rationally design allosteric drugs. For example, single-molecule experiments capture valuable information on a few important degrees of freedom and bulk experiments can provide coarse-grained energy landscapes but neither provides the atomistic structural information required for drug design. Crystallography captures such atomistic details but only for a small subset of the structures a protein can adopt. Room-temperature crystallography provides exciting insights into conformational heterogeneity. However, the requirement that crystals be able to withstand x-rays at room temperature makes sample preparation even more demanding than with standard cryogenic techniques, so it remains to be seen how broadly applicable this technique will be. NMR has the potential to capture some of the cryptic sites predicted by the disclosed model but the populations of many pockets are too small for NMR to detect. Coarse-grained simulations are computationally efficient but lack the structural detail required for drug design. For example, COREX/BEST is an Ising-like model that assumes continuous stretches of a protein's primary sequence are either folded or unfolded. This algorithm generates an ensemble of partially folded conformations that agrees well with hydrogen exchange data but there is no all atom representation of the ensemble to design drugs against. Methods like Rosetta provide atomically detailed models of different structures but do not provide the thermodynamic or kinetic information required to distinguish accessible conformations from inaccessible ones. Hypothetically, molecular dynamics simulations can provide this information. However, in practice, most biological processes are still beyond the reach of the most advanced sampling algorithms due to the number of atoms and the length of time that must be simulated.

Disclosed herein is an innovative combination of MSMs and experiments to leverage the conformational selection model to target cryptic sites. Combining these approaches will provide more rapid iterations of computational design and testing, leading to faster convergence on exciting new results. This work will greatly enhance the ability to identify and exploit cryptic sites.

The work on TEM-1 β-lactamase has revealed at least three cryptic pockets that are in communication with the active site. This Example sets out to definitively determine whether these sites have therapeutic value by designing and experimentally testing compounds that bind them. It is hypothesized that the majority of these compounds will alter the enzyme's activity by modulating the population of active enzyme and that inhibition will be easier to achieve than activation. This hypothesis is based on previous work demonstrating that all the cryptic pockets discovered in β-lactamase are in communication with the active site, thus ligand binding to these pockets is likely to perturb the enzyme's function. Furthermore, β-lactamase is a highly efficient enzyme, so it should be easier to inhibit it than to activate it. To test this hypothesis, software tools were developed for discovering small molecules that bind tightly to experimentally validated pockets that were observed in the structural ensembles. It was then experimentally tested whether the molecules allosterically inhibit the enzyme. To maximize the chance of success, a site-directed experimental screen that allows for the search of compounds that bind specific regions of a protein will also be employed, such as pockets revealed by the computational model and validated by the thiol-exchange experiments. Successful completion of this work will provide new starting points for future β-lactamase inhibitor development, which will establish the translational value of insights into proteins' conformational variability and spur similar studies into numerous other proteins.

Docking Successfully Retrodicts the Known Allosteric β-Lactamase Inhibitor.

As a first test of the potential for discovering allosteric modulators, Surflex-dock software was used to determine if the preferred binding site and binding mode of the known allosteric inhibitor can be retrodicted. First, a small library of compounds was compiled that included the known allosteric inhibitor, a known substrate (benzylpenicillin), and a hundred decoys selected from the eMolecules repository of commercially available compounds. Then the crystal structure with the known allosteric inhibitor bound in a cryptic site was modified to remove the small molecule, and both the active and allosteric sites in the remaining protein structure were used as targets for docking. Docking the small library against these two target sites correctly retrodicted that the known allosteric ligand prefers to bind the allosteric site over the active site, finding a binding pose within 0.33 Å of the crystallographic conformation. The known substrate preferred to bind in the active site over the allosteric site. Furthermore, both the allosteric compound and substrate scored better against their preferred sites than any of the decoy molecules. These results demonstrate that it is possible to identify allosteric modulators given knowledge of the different structures a protein adopts.

MSMs and Docking Successfully Predict New Target Conformations and Allosteric Modulators.

Figure 10A:
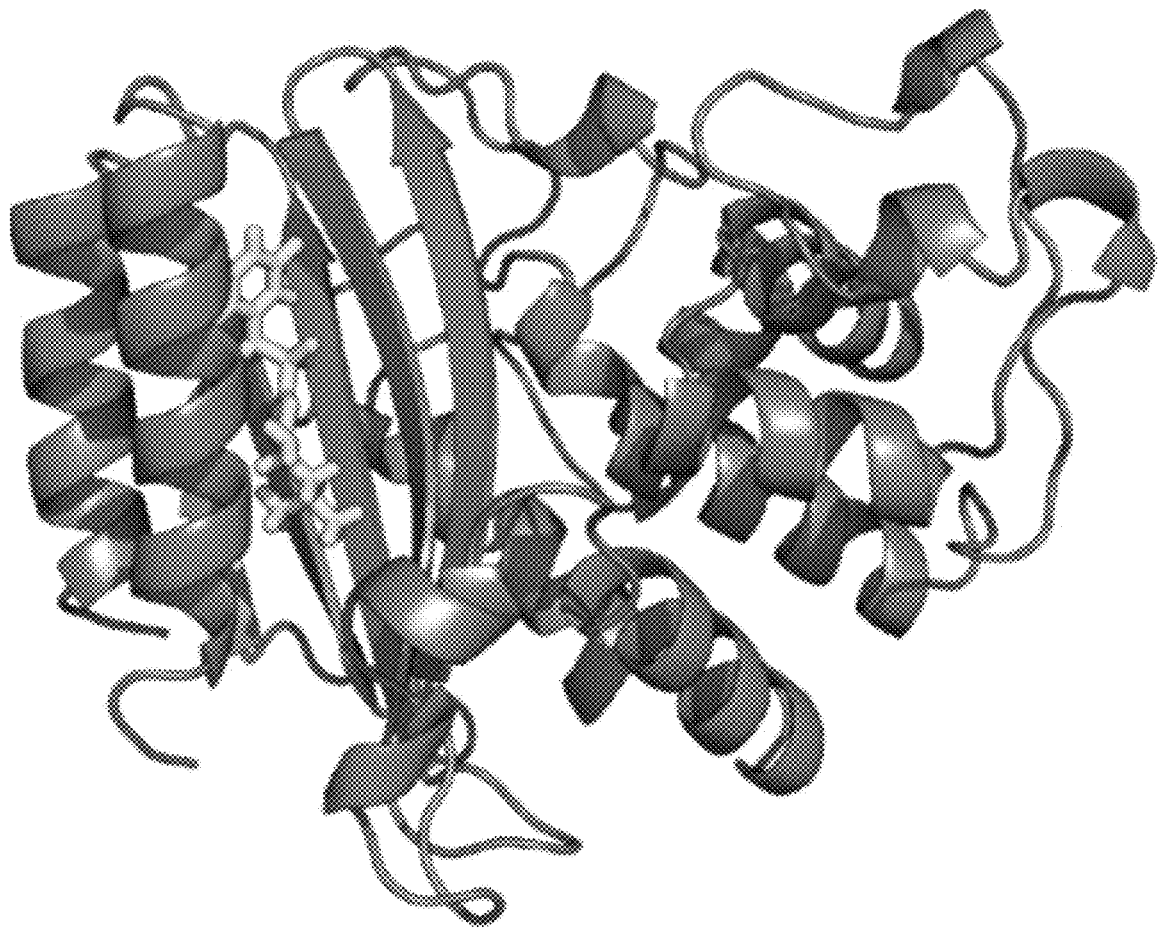
FIG. 10A depicts a model structure of an allosteric activator.
Figure 10B:
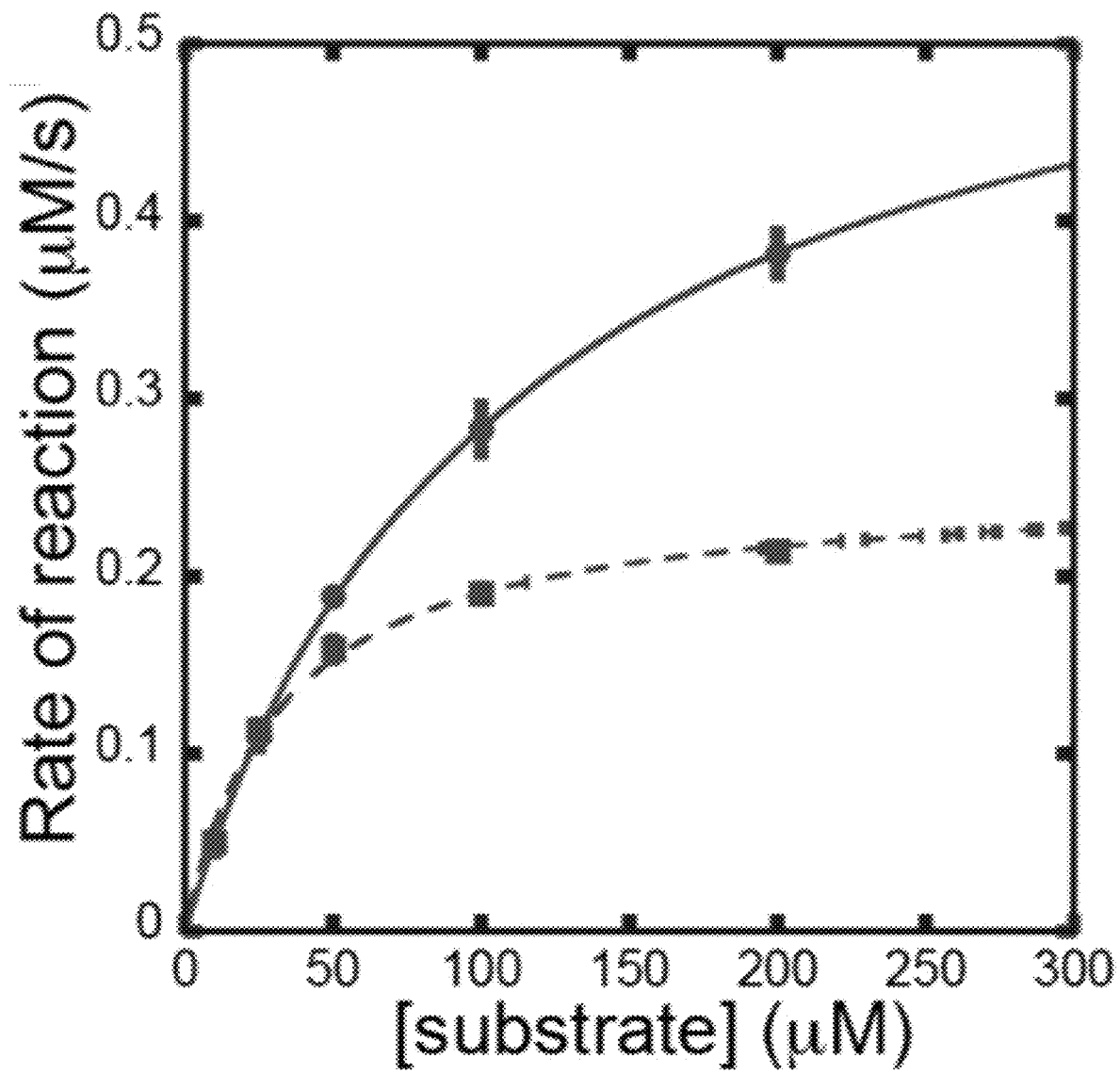
FIG. 10B depicts the enzyme kinetics with the activator (red diamonds, solid line) and without the activator (blue squares, dashed line). Lines are the Michaelis-Menten fit.

To test whether new allosteric modulators can be predicted, the largest pocket that is present in the model of TEM-1 β-lactamase was chosen as the target for docking. A library of ~60K compounds was prepared to dock against this structure and Surflex-dock was used to identify the ten compounds with the greatest potential to bind this pocket. This procedure revealed a promising compound, shown in FIG. 10A. To experimentally test this compound, the Michaelis-Menten kinetics of nitrocefin degradation by β-lactamase was measured both in the absence and presence of this compound. These experiments were performed in the presence of 0.01% triton to minimize the effects of aggregation. These experiments demonstrate that the predicted allosteric ligand increases both the $k_{cat}$ and KM for nitrocefin degradation (FIG. 10B) with a half-maximal effective concentration ($EC_{50}$) of 60 µM. This result is consistent with the prediction that the compound binds in an allosteric site since it is clearly not competing with the substrate for binding to the active site. It also establishes the capacity to find allosteric modulators using the current simulation and docking methods despite possible imperfections in the force fields for describing interatomic interactions. Other substrates are being evaluated to see if this compound increases their degradation and if saturating substrate concentrations can be reached to obtain precise $k_{cat}$ and KM values. Testing the top ten compounds also revealed a potential allosteric inhibitor, and experiments to determine if it is allosteric are described below.

Figure 11:
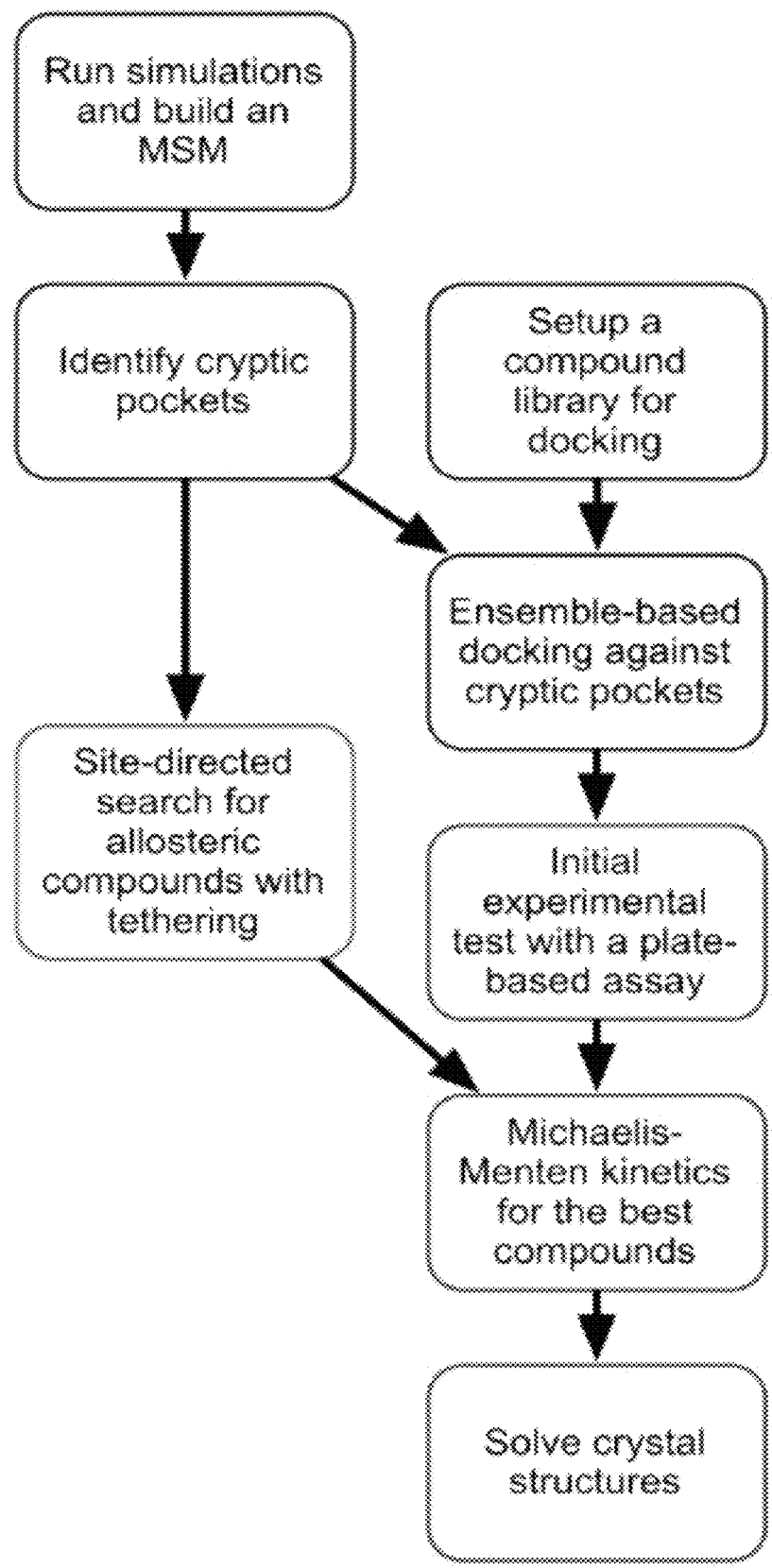
FIG. 11 depicts an experimental flow chart.

The structures of cryptic sites can be heterogeneous in the absence of a ligand, making it nontrivial to manually select specific structures to target. Therefore, new software tools for discovering drugs based on an entire ensemble of different structures will be developed, as outlined in FIG. 11.

Run Simulations and Build an MSM to Characterize Proteins' Structural Ensembles.

All simulations and modeling will be conducted using the same procedure used to build the model of TEM-1 β-lactamase. TEM-1 was simulated with the Gromacs software package with the Amber03 force field and TIP3P explicit solvent. This combination of software and parameters was selected because it has proven reliable in past studies of both protein folding and structural fluctuations within folded proteins. The MSMBuilder software package was used to build MSMs from the simulation data. First, the simulation data was clustered using the k-centers/k-medoids method, requiring that no two conformations in the same state have an RMSD between backbone heavy atoms and Cβ carbons greater than 1 Å. The validity of this model was checked with the implied timescales test. If a model failed this test, a smaller distance cutoff would be used for a new clustering. A matrix of transition probabilities between all pairs of states was then calculated using methods to infer the maximum likelihood transition matrix that satisfies microscopic reversibility and is consistent with the number of times each transition was observed in the simulations.

Identify Cryptic Pockets.

All the pockets that are present in representative structures for each state of the MSMs will be identified using the implementation of the LIGSITE algorithm. This algorithm works by dividing the system into a grid of 1 Å³ volume elements. For each volume element, it scans out along the x-, y-, and z-axes and each of the diagonals between these axes, resulting in a total of 9 scans for each volume element. Volume elements that are not filled by protein but are surrounded by protein atoms along at least four of these scans are designated as being part of a pocket. Contiguous pocket volumes are then grouped into one continuous pocket. To focus on druggable allosteric sites, the active site and any pockets that cannot encompass part of a small molecule will be discarded, as judged with a probe sphere with a radius of 3.4 Å.

Setup a Compound Library for Docking.

The National Cancer Institute (NCI) Developmental Therapeutics Program library will be used to search for potential allosteric modulators. This library contains ~250K compounds but it was filtered down to ~60K drug-like molecules by discarding compounds that are known to be promiscuous or that violate the following criteria for drug-likeness: masses between 200 and 400 Da., less than five hydrogen bond donors, less than 5 hydrogen bond acceptors, C Log P between 1 and 4.5, and less than 7 rotatable bonds. If allosteric modulators are not found in this library, then a larger library based on filtering the ~6M compounds in the eMolecules database would be searched.

Ensemble-Based Docking Against Cryptic Pockets.

The Surflex-dock software package with the standard high-resolution parameters to dock every compound in the library against each pocket discovered will be used to obtain a set of scores, s(struct,pocket,mol) where struct is a representative structure from one state in the MSM, pocket is a pocket in that structure, and mol is a chemical from the library. This score will be zero for any pocket that does not exist in a particular structure. A final score for each molecule will be calculated that captures the average affinity across the different structures of a pocket observed in the simulations ($s_{final}$(pocket,mol)=$\Sigma_{struct}$p(struct)×s(struct,pocket, mol) where p(struct) is the probability that the protein adopts a given structure from the MSM). This score will explicitly account for the protein's conformational entropy and the fact that different ligand conformations may bind more tightly to alternative protein structures. As demonstrated herein, any cryptic pocket in TEM-1 can communicate with the active site. Therefore, the simplifying assumption will be made that the molecules that bind most tightly to cryptic pockets are the most likely to alter the enzyme's activity. Mechanistic studies described below will allow better prediction as to whether a compound will activate or inhibit a protein and to what degree.

Working in an MSM framework provides a number of advantages over other methods for docking against structures from molecular dynamics simulations. For example, clustering a simulation dataset and docking against a representative structure for each cluster captures a diversity of potential bound structures but there is no way to judge whether a given protein structure is reasonably probable or if it is too high energy to be relevant. The MSM framework incorporates the equilibrium populations of each state, naturally favoring the compounds that bind most tightly to lower energy structures that are more accessible at thermal equilibrium.

Initial Experimental Test with a Plate-Based Assay.

A 96-well plate-based assay has been developed for measuring dose-dependent effects of compounds on the rate of TEM-1's enzymatic activity. With this assay, an initial test of the computational predictions can quickly be performed. Each compound is tested in triplicate at three different final concentrations: 50, 100, and 500 µM. For each plate, three wells for control runs with just buffer and substrate and three wells with buffer, substrate, and enzyme are used. This setup allows the testing of 10 compounds per plate. Each plate is setup with buffer and compound in each well and then a plate-reader with two injectors is used to introduce the enzyme and a nitrocefin substrate. The buffer includes 0.01% triton to prevent aggregation-induced inhibition. First, the enzyme (final concentration of 1 nM) is added and the compound and enzyme are allowed to equilibrate for five minutes. Then, a nitrocefin substrate is introduced (final concentration of 50 µM, which is near the $K_M$ for this substrate so that both competitive and non-competitive inhibition can be detected). Nitrocefin undergoes a colorimetric change upon cleavage. Compounds that alter the activity relative to the reference by greater than 20% will be followed up on.

More Detailed Kinetic Studies of the Best Compounds.

The effect of promising compounds on β-lactamase's Michaelis-Menten kinetics will be measured to quantify their potency and as an initial test of whether they are acting allosterically. For these measurements, a UV/Vis spectrophotometer is used to monitor the degradation of the same nitrocefin substrate used for the plate-based assays at substrate concentrations ranging from 10 nM to 200 nM. The concentration of the potential inhibitor/activator is based on the plate-based assay. Generally, the highest concentration of the allosteric effector where there is no visible aggregation is used. Compound stocks are made in DMSO and the final assay condition has 2% DMSO in the buffer. The buffer is identical to that for the plate-based assay, including 0.01% triton to prevent aggregation-induced inhibition. The resulting data is fit to the Michaelis-Menten model and the $k_{cat}$ and $K_M$ values are compared in the absence and presence of a potential inhibitor/activator. If the $k_{cat}$ is reduced but the $K_M$ is unchanged, then the inhibitor must be acting allosterically. Any activators are also likely to act allosterically. The $EC_{50}s$ for promising compounds will be measured by measuring the specific activities as the inhibitor/activator concentration is varied. For the most potent compounds that appear to be acting allosterically, crystal structures of the protein-ligand complex will be determined. Structures for efficacious compounds that cannot conclusively be classified as being allosteric or not may also be determined (e.g. because they are competitive or mixed inhibitors). Transient kinetics to obtain more mechanistic insights will also be measured.

Determine Crystal Structures for the Most Potent Hits to Definitively Determine where they Bind.

The crystal structures of protein-ligand complexes will be solved to test whether the computational models successfully predict where compounds bind. Published protocols for crystallizing TEM variants and for soaking native crystals with small molecules to solve ligand-bound structures will be used. Conditions for crystal growth and harvest will be optimized based on x-ray diffraction data collected from frozen crystals. High-resolution data will be collected at beam line 4.2.2 of the Advanced Light Source (ALS). Once native crystals are grown and the structure solved by molecular replacement, the lead compounds will be soaked or co-crystallized and the structures of the bound inhibitors solved. Surface entropy reduction mutant(s) could also be employed to improve crystallization behavior of the protein and to increase the probability that TEM-inhibitor complexes can be captured in an amenable crystal packing arrangement. If crystallized protein-ligand complexes are not obtained, the hydroxyl labeling technique will be used to determine where a compound binds by identifying the residues the compound protects from labeling.

What is claimed is:

1. A method of determining binding between a compound and a cryptic site within a protein of interest, the method comprising:
   a) contacting the cryptic site with the compound; and,
   b) measuring the binding of the compound to the cryptic site;
   wherein the compound has been predicted to bind to the cryptic site by a method comprising:
   i) automatically determining the different conformations the protein adopts using atomically-detailed molecular dynamics simulations to identify the structural states a protein populates, their equilibrium probabilities, and the rates of transitioning between them;
   ii) quantifying the relative probabilities that the protein adopts each of the conformations;
   iii) executing logic that docks each the compound against each conformation using a computing device;
   iv) automatically calculating an average score for the compound, wherein the score is weighted by the probability the protein adopts the conformation;
   v) automatically generating an output, wherein the output is a list of ranked compounds that effectively interact with the protein and
   vi) identifying a cryptic site in the protein of interest by steps i)-iv).

2. The method of claim 1, wherein the different conformations a protein adopts include hidden conformations.

3. The method of claim 1, wherein the relative probabilities are calculated based on the thermodynamics and kinetics of each conformation.

4. The method of claim 1, wherein the average score is the relative binding affinity of the compound.

5. The method of claim 1, wherein the average score is automatically calculated using the formula:

$$s_{final}(\text{pocket,mol}) = \Sigma_{struct} p(\text{struct}) \times s(\text{struct,pocket,mol})$$

wherein:
struct is a single conformation,
pocket is a pocket in the single conformation,
mol is a compound,
p(struct) is the probability that the protein adopts the single conformation, and
$s_{final}$(pocket,mol) is a final score for the compound that captures the average affinity across the different conformations of a pocket observed.

6. The method of claim 1, wherein one or more compounds effectively interact with any site on a protein, including an active site, protein-ligand interaction site, or cryptic pocket on the protein of interest.

7. The method of claim 1, wherein the compound is a competitive inhibitor, an allosteric inhibitor or allosteric activator.

8. The method of claim 1, wherein more than 10 different conformations are determined.

9. The method of claim 1, wherein more than 100 different conformations are determined.

10. The method of claim 1, wherein more than 1000 different conformations are determined.

11. The method of claim 1, wherein more than 2000 different conformations are determined.

12. The method of claim 1, wherein more than 6000 different conformations are determined.

13. The method of claim 1, wherein more than 100,000 different conformations are determined.

* * * * *